United States Patent
McCormack et al.

(10) Patent No.: US 7,220,478 B2
(45) Date of Patent: May 22, 2007

(54) MICROPOROUS BREATHABLE ELASTIC FILMS, METHODS OF MAKING SAME, AND LIMITED USE OR DISPOSABLE PRODUCT APPLICATIONS

(75) Inventors: Ann Louise McCormack, Cumming, GA (US); Susan Elaine Shawver, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 414 days.

(21) Appl. No.: 10/703,761

(22) Filed: Nov. 7, 2003

(65) Prior Publication Data
US 2005/0043460 A1  Feb. 24, 2005

Related U.S. Application Data

(63) Continuation-in-part of application No. 10/646,978, filed on Aug. 22, 2003, now abandoned.

(51) Int. Cl.
- B32B 5/16   (2006.01)
- B32B 27/20  (2006.01)
- C08J 3/20   (2006.01)
- C08K 3/26   (2006.01)

(52) U.S. Cl. .............. 428/304.4; 428/317.9; 428/323; 428/500; 428/910; 524/425; 524/445; 524/492

(58) Field of Classification Search ............ None
See application file for complete search history.

(56) References Cited

U.S. PATENT DOCUMENTS

| 3,046,172 A | 7/1962 | Reid |
| 3,233,029 A | 2/1966 | Rasmussen |
| 3,276,944 A | 10/1966 | Levy |
| 3,338,992 A | 8/1967 | Kinney |
| 3,341,394 A | 9/1967 | Kinney |
| 3,383,449 A | 5/1968 | Muller |
| 3,502,538 A | 3/1970 | Petersen |
| 3,502,763 A | 3/1970 | Hartmann |

(Continued)

FOREIGN PATENT DOCUMENTS

CA          803714        1/1969

(Continued)

OTHER PUBLICATIONS

Encyclopedia of Polymer Science and Engineering, Wiley & Sons, vol. 10, 211-212, 1987.

(Continued)

*Primary Examiner*—Monique R. Jackson
(74) *Attorney, Agent, or Firm*—Steven D. Flack; Richard M. Shane; James Arnold, Jr.

(57) ABSTRACT

A thermoplastic elastomer film includes a thermoplastic elastomer and a filled semi crystalline predominantly linear polymer. The film includes between about 25 and 70 weight percent filler, between about 5 and 30 by weight percent semi-crystalline linear polymer, and between about 15 and 60 by weight elastomer. The filler is closely associated with the semi-crystalline linear polymer. The elastic film demonstrates a load loss value at a 50 percent elongation of less than about 50 percent, and a breathability of greater than about 100 g/m²/24 hours.

50 Claims, 5 Drawing Sheets

U.S. PATENT DOCUMENTS

| | | |
|---|---|---|
| 3,542,615 A | 11/1970 | Dobo et al. |
| 3,676,242 A | 7/1972 | Prentice |
| 3,692,618 A | 9/1972 | Dorschner et al. |
| 3,761,348 A | 9/1973 | Chamberlin |
| 3,802,817 A | 4/1974 | Matsuki et al. |
| 3,839,240 A | 10/1974 | Zimmerman |
| 3,844,865 A | 10/1974 | Elton et al. |
| 3,849,241 A | 11/1974 | Butin et al. |
| 3,849,526 A | 11/1974 | Muller et al. |
| 3,855,046 A | 12/1974 | Hansen et al. |
| 3,870,593 A | 3/1975 | Elton et al. |
| 3,880,966 A | 4/1975 | Zimmerman et al. |
| 3,988,883 A | 11/1976 | Sze |
| 4,039,364 A | 8/1977 | Rasmussen |
| 4,041,203 A | 8/1977 | Brock et al. |
| 4,100,324 A | 7/1978 | Anderson et al. |
| 4,106,313 A | 8/1978 | Boe |
| 4,116,892 A | 9/1978 | Schwarz |
| 4,136,218 A | 1/1979 | Nischwitz et al. |
| 4,138,459 A | 2/1979 | Brazinsky et al. |
| 4,144,008 A | 3/1979 | Schwarz |
| 4,153,664 A | 5/1979 | Sabee |
| 4,153,751 A | 5/1979 | Schwarz |
| 4,223,059 A | 9/1980 | Schwarz |
| 4,243,802 A | 1/1981 | Landoll |
| 4,251,585 A | 2/1981 | Schwarz |
| 4,265,960 A | 5/1981 | Arbit et al. |
| 4,285,100 A | 8/1981 | Schwarz |
| 4,289,832 A | 9/1981 | Schwarz |
| 4,301,102 A | 11/1981 | Fernstrom et al. |
| 4,336,638 A | 6/1982 | Mercer |
| 4,340,563 A | 7/1982 | Appel et al. |
| 4,350,655 A | 9/1982 | Hoge |
| 4,364,985 A | 12/1982 | Tokuyama et al. |
| 4,368,565 A | 1/1983 | Schwarz |
| 4,374,175 A | 2/1983 | Tanaka |
| 4,374,888 A | 2/1983 | Bornslaeger |
| 4,384,023 A | 5/1983 | Okamura et al. |
| 4,405,686 A | 9/1983 | Kuroda et al. |
| 4,422,892 A | 12/1983 | Plant |
| 4,424,257 A | 1/1984 | Bach |
| 4,438,167 A | 3/1984 | Schwarz |
| 4,443,513 A | 4/1984 | Meitner et al. |
| 4,464,815 A | 8/1984 | Canterino et al. |
| 4,472,328 A | 9/1984 | Sugimoto et al. |
| 4,475,971 A | 10/1984 | Canterino |
| 4,517,714 A | 5/1985 | Sneed et al. |
| 4,521,484 A | 6/1985 | Li |
| 4,522,203 A | 6/1985 | Mays |
| 4,533,510 A | 8/1985 | Nissel |
| 4,563,229 A | 1/1986 | Sorez |
| 4,590,124 A | 5/1986 | Schoenberg |
| 4,613,643 A | 9/1986 | Nakamura et al. |
| 4,629,525 A | 12/1986 | Rasmussen |
| 4,663,220 A | 5/1987 | Wisneski et al. |
| 4,698,372 A | 10/1987 | Moss |
| 4,701,432 A | 10/1987 | Welborn, Jr. |
| 4,720,415 A | 1/1988 | Vander Wielen et al. |
| 4,734,324 A | 3/1988 | Hill |
| 4,758,239 A | 7/1988 | Yeo et al. |
| 4,777,073 A | 10/1988 | Sheth |
| 4,789,699 A | 12/1988 | Kieffer et al. |
| 4,793,885 A | 12/1988 | Rasmussen |
| 4,795,668 A | 1/1989 | Krueger et al. |
| 4,806,300 A | 2/1989 | Walton et al. |
| 4,816,094 A | 3/1989 | Pomplun et al. |
| 4,818,464 A | 4/1989 | Lau |
| 4,820,590 A | 4/1989 | Hodgson, Jr. et al. |
| 4,833,172 A | 5/1989 | Schwarz et al. |
| 4,854,995 A | 8/1989 | Kasper et al. |
| 4,861,660 A | 8/1989 | Ishii |
| 4,863,785 A | 9/1989 | Berman et al. |
| 4,867,881 A | 9/1989 | Kinzer |
| 4,877,679 A | 10/1989 | Leatherman et al. |
| 4,923,650 A | 5/1990 | Antoon, Jr. et al. |
| 4,965,122 A | 10/1990 | Morman |
| 4,972,522 A | 11/1990 | Rautenberg |
| 4,981,747 A | 1/1991 | Morman |
| 4,992,124 A | 2/1991 | Kurihara et al. |
| 4,994,335 A | 2/1991 | Kamaei et al. |
| 5,011,698 A | 4/1991 | Antoon, Jr. et al. |
| 5,028,289 A | 7/1991 | Rasmussen |
| 5,057,368 A | 10/1991 | Largman et al. |
| 5,064,802 A | 11/1991 | Stevens et al. |
| 5,069,970 A | 12/1991 | Largman et al. |
| 5,073,316 A | 12/1991 | Bizen et al. |
| 5,108,820 A | 4/1992 | Kaneko et al. |
| 5,108,827 A | 4/1992 | Gessner |
| 5,116,662 A | 5/1992 | Morman |
| 5,117,540 A | 6/1992 | Walton et al. |
| 5,120,594 A | 6/1992 | Mrozinski |
| 5,143,679 A | 9/1992 | Weber et al. |
| 5,145,727 A | 9/1992 | Potts et al. |
| 5,153,254 A | 10/1992 | Chen |
| 5,156,793 A | 10/1992 | Buell et al. |
| 5,164,258 A | 11/1992 | Shida et al. |
| 5,167,897 A | 12/1992 | Weber et al. |
| 5,169,706 A | 12/1992 | Collier, IV et al. |
| 5,169,712 A | 12/1992 | Tapp |
| 5,176,953 A | 1/1993 | Jacoby et al. |
| 5,178,931 A | 1/1993 | Perkins et al. |
| 5,188,885 A | 2/1993 | Timmons et al. |
| 5,204,429 A | 4/1993 | Kaminsky et al. |
| 5,226,992 A | 7/1993 | Morman |
| 5,238,623 A | 8/1993 | Mrozinski |
| 5,256,231 A | 10/1993 | Gorman et al. |
| 5,256,417 A | 10/1993 | Koltisko |
| 5,271,883 A | 12/1993 | Timmons et al. |
| 5,277,976 A | 1/1994 | Hogle et al. |
| 5,288,791 A | 2/1994 | Collier, IV et al. |
| 5,294,482 A | 3/1994 | Gessner |
| 5,296,184 A | 3/1994 | Wu et al. |
| 5,304,599 A | 4/1994 | Himes |
| 5,332,613 A | 7/1994 | Taylor et al. |
| 5,336,545 A | 8/1994 | Morman |
| 5,336,552 A | 8/1994 | Strack et al. |
| 5,352,518 A | 10/1994 | Muramoto et al. |
| 5,370,940 A | 12/1994 | Hazlitt et al. |
| 5,374,696 A | 12/1994 | Rosen et al. |
| 5,376,430 A | 12/1994 | Swenson et al. |
| 5,380,313 A | 1/1995 | Goulait et al. |
| 5,380,578 A | 1/1995 | Rautenberg |
| 5,382,400 A | 1/1995 | Pike et al. |
| 5,393,599 A | 2/1995 | Quantrille et al. |
| 5,395,810 A | 3/1995 | Shamshoum et al. |
| 5,405,887 A | 4/1995 | Morita et al. |
| 5,411,636 A | 5/1995 | Hermans et al. |
| 5,418,045 A | 5/1995 | Pike et al. |
| 5,424,025 A | 6/1995 | Hanschen et al. |
| 5,425,987 A | 6/1995 | Shawver et al. |
| 5,429,856 A | 7/1995 | Krueger et al. |
| 5,451,450 A | 9/1995 | Erderly et al. |
| 5,455,992 A | 10/1995 | Kurschatke et al. |
| 5,456,982 A | 10/1995 | Hansen et al. |
| 5,466,410 A | 11/1995 | Hills |
| 5,468,702 A | 11/1995 | Jejelowo |
| 5,472,775 A | 12/1995 | Obijeski et al. |
| 5,489,469 A | 2/1996 | Kobayashi et al. |
| 5,492,598 A | 2/1996 | Hermans et al. |
| 5,498,468 A | 3/1996 | Blaney |
| 5,501,679 A | 3/1996 | Krueger et al. |
| RE35,206 E | 4/1996 | Hassenboehler, Jr. et al. |
| 5,514,470 A | 5/1996 | Haffner et al. |
| 5,514,634 A | 5/1996 | Hagerty et al. |

| | | | | | | |
|---|---|---|---|---|---|---|
| 5,518,801 | A | 5/1996 | Chappell et al. | 6,172,177 | B1 | 1/2001 | Wang et al. |
| 5,527,752 | A | 6/1996 | Reichle et al. | 6,174,602 | B1 | 1/2001 | Matsui et al. |
| H1558 | H | 7/1996 | Goulait et al. | 6,179,939 | B1 | 1/2001 | Jones, Jr. et al. |
| 5,539,124 | A | 7/1996 | Etherton et al. | 6,190,758 | B1 | 2/2001 | Stopper |
| 5,540,976 | A | 7/1996 | Shawver et al. | 6,203,654 | B1 | 3/2001 | McFall et al. |
| 5,540,992 | A | 7/1996 | Marcher et al. | 6,204,208 | B1 | 3/2001 | Krzysik et al. |
| 5,554,775 | A | 9/1996 | Krishnamurti et al. | 6,214,274 | B1 | 4/2001 | Melius et al. |
| 5,576,374 | A | 11/1996 | Betso et al. | 6,225,243 | B1 | 5/2001 | Austin |
| 5,599,420 | A | 2/1997 | Yeo et al. | 6,242,041 | B1 | 6/2001 | Katoot et al. |
| 5,604,036 | A | 2/1997 | Price et al. | 6,242,084 | B1 | 6/2001 | Peet |
| 5,614,281 | A | 3/1997 | Jackson et al. | 6,258,308 | B1 | 7/2001 | Brady et al. |
| 5,624,427 | A | 4/1997 | Bergman et al. | 6,264,864 | B1 | 7/2001 | Mackay |
| 5,628,097 | A | 5/1997 | Benson et al. | 6,265,045 | B1 | 7/2001 | Mushaben |
| 5,643,846 | A | 7/1997 | Reddy et al. | 6,268,062 | B1 | 7/2001 | DeMeuse |
| 5,648,428 | A | 7/1997 | Reddy et al. | 6,270,912 | B1 | 8/2001 | Peet |
| 5,650,225 | A | 7/1997 | Dutta et al. | 6,309,736 | B1 | 10/2001 | McCormack et al. |
| 5,651,853 | A | 7/1997 | Wrigley et al. | 6,329,454 | B1 | 12/2001 | Krabbenborg |
| 5,661,096 | A | 8/1997 | Winter et al. | 6,355,200 | B1 | 3/2002 | Schmidt et al. |
| 5,665,083 | A | 9/1997 | Igaue et al. | 6,383,431 | B1 | 5/2002 | Dobrin et al. |
| 5,690,627 | A | 11/1997 | Clear et al. | 6,399,531 | B1 | 6/2002 | Job et al. |
| 5,691,034 | A | 11/1997 | Krueger et al. | 6,403,717 | B1 | 6/2002 | Adams et al. |
| 5,695,376 | A | 12/1997 | Datta et al. | 6,409,711 | B1 | 6/2002 | Jönbrink |
| 5,695,377 | A | 12/1997 | Triebes et al. | 6,444,302 | B1 | 9/2002 | Srinivas et al. |
| 5,695,868 | A | 12/1997 | McCormack | 6,461,457 | B1 | 10/2002 | Taylor et al. |
| 5,707,468 | A | 1/1998 | Arnold et al. | 6,475,591 | B2 | 11/2002 | Mushaben |
| 5,723,087 | A | 3/1998 | Chappell et al. | 6,479,154 | B1 | 11/2002 | Walton et al. |
| 5,723,546 | A | 3/1998 | Sustic | 6,481,483 | B1 | 11/2002 | Kobayashi et al. |
| 5,733,628 | A | 3/1998 | Pelkie | 6,518,208 | B2 | 2/2003 | Terakawa |
| 5,735,840 | A | 4/1998 | Kline et al. | 6,586,354 | B1 | 7/2003 | Topolkaraev et al. |
| 5,743,999 | A | 4/1998 | Kamps et al. | 6,680,265 | B1 | 1/2004 | Smith et al. |
| 5,747,405 | A | 5/1998 | Little et al. | 6,706,228 | B2 | 3/2004 | Mackay |
| 5,755,902 | A | 5/1998 | Reynolds | 6,794,024 | B1 | 9/2004 | Walton et al. |
| 5,756,580 | A | 5/1998 | Natori et al. | 6,881,375 | B2 | 4/2005 | Topolkaraev et al. |
| 5,758,842 | A | 6/1998 | Dorfel et al. | 6,896,843 | B2 | 5/2005 | Topolkaraev et al. |
| 5,759,926 | A | 6/1998 | Pike et al. | 6,969,378 | B1 | 11/2005 | Vukos et al. |
| 5,763,334 | A | 6/1998 | Gupta et al. | 2001/0041487 | A1 | 11/2001 | Brady et al. |
| 5,770,531 | A | 6/1998 | Sudduth et al. | 2001/0042938 | A1 | 11/2001 | Mackay |
| 5,789,065 | A | 8/1998 | Haffner et al. | 2002/0004350 | A1 | 1/2002 | Morman et al. |
| 5,804,524 | A | 9/1998 | Reddy et al. | 2002/0006482 | A1 | 1/2002 | Falla et al. |
| 5,814,390 | A | 9/1998 | Stokes et al. | 2002/0088534 | A1 | 7/2002 | Kobayashi et al. |
| 5,814,567 | A | 9/1998 | Yahiaoui et al. | 2002/0105110 | A1 | 8/2002 | Dobrin et al. |
| 5,846,365 | A | 12/1998 | Kline et al. | 2002/0111598 | A1 | 8/2002 | Vogt et al. |
| 5,853,635 | A | 12/1998 | Morell et al. | 2002/0117770 | A1 | 8/2002 | Haynes et al. |
| 5,853,638 | A | 12/1998 | Han | 2002/0182426 | A1 | 12/2002 | Tanaka et al. |
| 5,883,028 | A | 3/1999 | Morman et al. | 2003/0045844 | A1 | 3/2003 | Taylor et al. |
| 5,885,908 | A | 3/1999 | Jaeger et al. | 2003/0050618 | A1 | 3/2003 | Kondo et al. |
| 5,888,607 | A | 3/1999 | Seth et al. | 2003/0065297 | A1 | 4/2003 | Davis et al. |
| 5,900,306 | A | 5/1999 | Stopper | 2003/0071391 | A1 | 4/2003 | Brady et al. |
| 5,910,136 | A | 6/1999 | Hetzler et al. | 2003/0125696 | A1 | 7/2003 | Morman et al. |
| 5,914,084 | A | 6/1999 | Benson et al. | 2004/0021251 | A1 | 2/2004 | Wheat et al. |
| 5,928,211 | A | 7/1999 | Gustafsson et al. | 2004/0087235 | A1 | 5/2004 | Morman et al. |
| 5,928,212 | A | 7/1999 | Kline et al. | 2004/0091752 | A1 | 5/2004 | Morman et al. |
| 5,945,175 | A | 8/1999 | Yahiaoui et al. | 2004/0110442 | A1 | 6/2004 | Rhim et al. |
| 5,957,907 | A | 9/1999 | Sauer | 2004/0122408 | A1 | 6/2004 | Potnis et al. |
| 5,972,502 | A | 10/1999 | Jessee et al. | 2004/0127131 | A1 | 7/2004 | Potnis |
| 5,984,911 | A | 11/1999 | Siebers et al. | 2005/0042962 | A1 | 2/2005 | McCormack et al. |
| 5,993,589 | A | 11/1999 | Morman | 2005/0101206 | A1 | 5/2005 | McCormack et al. |
| 6,015,764 | A | 1/2000 | McCormack et al. | | | | |
| 6,017,832 | A | 1/2000 | Yahiaoui et al. | | FOREIGN PATENT DOCUMENTS | | | |
| 6,028,016 | A | 2/2000 | Yahiaoui et al. | | | | |
| 6,037,417 | A | 3/2000 | Nguyen et al. | DE | | 2503775 | 8/1976 |
| 6,045,900 | A | 4/2000 | Haffner et al. | DE | | 25 13 251 | 9/1976 |
| 6,054,002 | A | 4/2000 | Griesbach et al. | DE | | 19833661 | 8/1999 |
| 6,072,005 | A | 6/2000 | Kobylivker et al. | EP | | 0 068 659 | 1/1983 |
| 6,075,179 | A | 6/2000 | McCormack et al. | EP | | 0 064 853 | 7/1986 |
| 6,096,014 | A | 8/2000 | Haffner et al. | EP | | 0 090 380 | 12/1990 |
| 6,106,956 | A | 8/2000 | Heyn et al. | EP | | 419 742 | 4/1991 |
| 6,111,163 | A | 8/2000 | McCormack et al. | EP | | 432 755 | 6/1991 |
| 6,114,024 | A | 9/2000 | Forte | EP | | 0 341 993 | 8/1993 |
| 6,120,899 | A | 9/2000 | Cameron et al. | EP | | 0556749 | 8/1993 |
| 6,135,987 | A | 10/2000 | Tsai et al. | EP | | 602 613 | 6/1994 |
| 6,156,421 | A | 12/2000 | Stopper et al. | EP | | 0 276 100 | 8/1994 |
| 6,169,045 | B1 | 1/2001 | Pike et al. | EP | | 0 575 509 | 10/1994 |

| | | |
|---|---|---|
| EP | 0 379 763 | 12/1994 |
| EP | 0 370 835 | 12/1995 |
| EP | 452727 | 3/1996 |
| EP | 0754544 A2 | 1/1997 |
| EP | 0 409 315 | 5/1997 |
| EP | 0 573 586 | 5/1997 |
| EP | 800 808 | 10/1997 |
| EP | 0 829 566 | 3/1998 |
| EP | 0 551 327 | 6/1998 |
| EP | 0 714 351 | 12/1998 |
| EP | 0 712 304 | 4/1999 |
| EP | 0 782 639 | 10/1999 |
| EP | 0 676 418 | 7/2000 |
| EP | 1 066 962 | 1/2001 |
| EP | 1 068 853 | 1/2001 |
| EP | 1 151 846 | 11/2001 |
| EP | 0 747 402 | 12/2001 |
| EP | 1 091 968 | 1/2002 |
| EP | 0 852 483 | 4/2002 |
| EP | 0 927 096 | 5/2002 |
| EP | 1 216 135 | 5/2003 |
| EP | 1 335 057 | 8/2003 |
| GB | 1521579 | 8/1978 |
| GB | 1526722 | 9/1978 |
| GB | 1526723 | 9/1978 |
| GB | 1526724 | 9/1978 |
| GB | 1553102 | 9/1979 |
| GB | 1579718 | 11/1980 |
| GB | 1598737 | 9/1981 |
| GB | 1598738 | 9/1981 |
| GB | 2 103 537 | 2/1983 |
| GB | 2 115 702 | 9/1983 |
| GB | 2284538 | 6/1995 |
| GB | 2310606 | 9/1997 |
| GB | 2325146 | 11/1998 |
| JP | 60-194947 | 10/1985 |
| JP | 62-078214 | 4/1987 |
| JP | 03-192132 | 8/1991 |
| JP | 07-002922 | 1/1995 |
| JP | 08-003203 | 1/1996 |
| JP | 08-041118 | 2/1996 |
| JP | 08-231625 | 9/1996 |
| JP | 09-241961 | 9/1997 |
| JP | 2001261868 | 9/2001 |
| JP | 2002069812 | 3/2002 |
| WO | WO 92/01401 | 2/1992 |
| WO | WO 93/15251 | 8/1993 |
| WO | WO 2004/020174 | 8/1993 |
| WO | 94/00292 | 1/1994 |
| WO | WO 96/19346 | 6/1996 |
| WO | WO 97/02133 | 1/1997 |
| WO | WO 97/04955 | 2/1997 |
| WO | WO 97/29909 | 8/1997 |
| WO | WO 97/45259 | 12/1997 |
| WO | WO 97/49848 | 12/1997 |
| WO | 98/02610 | 1/1998 |
| WO | WO 98/04397 | 2/1998 |
| WO | WO 98/05501 | 2/1998 |
| WO | WO 98/05502 | 2/1998 |
| WO | WO 98/23804 | 6/1998 |
| WO | 98/29481 | 7/1998 |
| WO | 98/29504 | 7/1998 |
| WO | WO 98/29239 | 7/1998 |
| WO | WO 98/29480 | 7/1998 |
| WO | WO 98/31318 | 7/1998 |
| WO | WO 98/48091 | 10/1998 |
| WO | WO 98/51475 | 11/1998 |
| WO | WO 98/58799 | 12/1998 |
| WO | WO 99/14039 | 3/1999 |
| WO | WO 99/14044 | 3/1999 |
| WO | WO 99/14046 | 3/1999 |
| WO | WO 99/14262 | 3/1999 |
| WO | WO 99/37840 | 7/1999 |
| WO | WO 99/49833 | 7/1999 |
| WO | WO 99/42068 | 8/1999 |
| WO | WO 99/47590 | 9/1999 |
| WO | WO 00/08243 | 2/2000 |
| WO | WO 00/23255 | 4/2000 |
| WO | WO 00/23509 | 4/2000 |
| WO | WO 00/28123 | 5/2000 |
| WO | WO 00/29199 | 5/2000 |
| WO | WO 00/48834 | 8/2000 |
| WO | WO 00/56522 | 9/2000 |
| WO | WO 00/69383 | 11/2000 |
| WO | WO 00/69615 | 11/2000 |
| WO | WO 00/76445 | 12/2000 |
| WO | WO 00/76446 | 12/2000 |
| WO | WO 01/00398 | 1/2001 |
| WO | WO 01/12306 | 2/2001 |
| WO | WO 01/14627 | 3/2001 |
| WO | WO 01/16219 | 3/2001 |
| WO | WO 01/19592 | 3/2001 |
| WO | WO 01/23180 | 4/2001 |
| WO | WO 01/32116 | 5/2001 |
| WO | WO 01/40358 | 6/2001 |
| WO | WO 01/47710 | 7/2001 |
| WO | WO 01/83210 | 11/2001 |
| WO | WO 01/83599 | 11/2001 |
| WO | WO 02/100207 | 12/2002 |
| WO | WO 02/102592 | 12/2002 |
| WO | WO 03/028606 | 4/2003 |
| WO | WO 03/057106 A1 | 7/2003 |
| WO | WO 03/072338 | 9/2003 |

OTHER PUBLICATIONS

*Polymer Blends and Composites*, John A. Manson and Leslie H. Sperling, copyright 1976, Plenum Press, ISBN-0-306-30831-2, pp. 273-277.

INDA (Association of the Nonwoven Fabrics Industry) No. IST-70.4-99, entitled "Standard Test Method for Water Vapor Transmission Rate Through Nonwoven and Plastic Film Using a Guard Film and Vapor Pressure Sensor".

NRL Report 4364, "Manufacture of Super-Fine Organic Fibers" by V. A. Wente, E. L. Boone and C. D. Fluharty, May 25, 1954.

NRL Report 5265, "An Improved Device For The Formation of Super-Fine Thermoplastic Fibers" by K.D. Lawrence, R. T. Lukas, J. A. Young.

ASTM D882-97, "Standard Test Method for Tensile Properties of Thin Plastic Sheeting", pp. 159-167, Apr. 1998.

Kirk-Othmer, Encyclopedia of Chemical Technology, Fourth Edition, John Wiley & Sons, Inc., New York, vol. 17, 765-767, 1996.

"Fibers," Cargill Dow, Internet web page, "http://www.cargilldow.com/fibers.asp", viewed and printed Jul. 23, 2002, pp. 1-4.

"PLA Processing Guide for Bulked Continuous Filament (BCF)," Cargill Dow, Internet web page, "http://www.cargilldow.com/pdf/fiberguide.html", viewed and printed Jul. 23, 2002, pp. 1-3.

Lunt, James and Andrew L. Shafer, "Polylactic Acid Polymers from Corn Potential Applications in the Textiles Industry," *Journal of Industrial Textiles*, vol. 29, No. 3, Jan. 2000, pp. 191-205 (reprint pp. 1-8).

US 5,242,876, 09/1993, Shamshoum et al. (withdrawn)

MICROPOROUS BREATHABLE ELASTIC FILMS, METHODS OF MAKING SAME, AND LIMITED USE OR DISPOSABLE PRODUCT APPLICATIONS

This application is a continuation in part of and claims priority from U.S. patent application bearing, and bearing Ser. No. 10/646,978, titled Microporous Breathable Elastic Films, Methods of Making Same, and Limited Use or Disposable Product Applications, to Ann Louise McCormack et al. filed on Aug. 22, 2003 now abandoned. The foregoing Application is incorporated by reference in its entirety.

FIELD OF THE INVENTION

The present invention relates to elastic films and laminates made therefrom, manufacturing methods for making such films, and disposable product applications of such films.

BACKGROUND OF THE INVENTION

Film and film/nonwoven laminates are used in a wide variety of applications, not the least of which is as outercovers/backsheets for limited use or disposable products including personal care absorbent articles such as diapers, training pants, swimwear, incontinence garments, feminine hygiene products, wound dressings, bandages and the like. Film/nonwoven laminates also have applications in the protective cover area, such as car, boat or other object cover components, tents (outdoor recreational covers), and in the health care area in conjunction with such products as surgical drapes, hospital gowns and fenestration reinforcements. Additionally, such materials have applications in other apparel for clean room, health care and other uses such as agricultural fabrics (row covers).

In the personal care area in particular, there has been an emphasis on the development of film laminates which have good barrier properties, especially with respect to liquids, as well as good aesthetic and tactile properties such as hand and feel. There has been a further emphasis on the "stretch" comfort of such laminates, that is, the ability of the laminates to "give" as a result of the product utilizing such laminates being elongated in use, but also to provide a necessary level of vapor permeability to maintain skin health of a product user.

It is known that breathable polymeric films may be made by utilizing a variety of thermoplastic polymers in combinations with filler particles. These and other desired components, such as additives can be mixed together, heated and then extruded into a monolayer or multilayer filled film. Examples are described in WO 96/19346 to McCormack et al., incorporated by reference herein in its entirety. The filled film may be made by any one of a variety of film forming processes known in the art such as, for example, by using either cast or blown film equipment. The thermoplastic film can then be stretched either alone or as part of a laminate to impart breathability or other desired properties. The films are often stretched in a machine direction orienter-type apparatus, or other stretching device, which stretches the film, thereby creating a pore-like matrix in the film body at the locations of the filler particles. While such breathable films and film/laminates are known to be used as personal care outercover materials, thereby allowing the personal care products to "breathe" and making such products more comfortable to wear, there has been difficulty producing such materials from "elastic" -type materials. Often, such breathable films are produced from polyolefin materials that can be extended without the ability to retract. While such film materials offer the comfort of air/gas circulation, and may offer the ability to extend only, they may limit or restrict movement of a user wearing articles made from such materials. If they are extended to a great extent, they may sag within the product, since they lack the ability to retract, and may in some circumstances, contribute to leakage. Such sagging sacrifices both the aesthetic appearance and the comfort level of the product.

It is has been found that if filler is placed in elastic polymer film formulations, the pores that are formed around the filler particles during a film formation stretch operation (such as in a machine direction orienter) are temporary, and close after stretching, as a result of the elastic attributes of the polymer component in the film. Without the pore structures, the film becomes non-breathable. It therefore is widely recognized that properties relating to elasticity and breathability are often conflicting. As a result of these attributes of highly elastic polymers, when breathable and elastic film materials have been sought for personal care product applications, manufacturers have often turned to inherently breathable elastic materials, that allow gasses to pass or diffuse through their structures, without the necessity for pores (which risk collapse). Such inherently breathable films may be more costly than other material films, often do not provide the level of breathability desired for consumer product applications, and often have to be fairly thin in order to achieve an acceptable level of breathability. Such thin films often lack the requisite strength/tear strength characteristics desired in personal care products.

It would therefore be desirable to produce filled breathable elastic films of varying basis weights, without the risk of pore collapse. It would further be desirable to produce breathable elastic films that may be efficiently laminated to nonwoven sheet structures without sacrificing elastic functionality. It is to such needs that the present invention is directed.

SUMMARY OF THE INVENTION

A method for forming an elastic, breathable film includes the steps of filling a semi-crystalline, predominantly linear polymer with a filler to form a filled polymer such that the filled polymer contains at least 60 percent by weight and desirably at least 70 percent by weight filler; dry-blending a thermoplastic elastomer with the filled polymer to form a blended elastomer composition, such that the blended elastomer composition includes between about 25 and 70 percent filler by weight, between about 5 and 30 percent semi-crystalline polymer by weight, and between about 15 and 60 percent by weight elastomer; extruding the blended elastomer composition into a film; orienting the film in a machine direction between about 2 and 5 times, such that the film produced has a basis weight of between about 15 and 60 gsm and demonstrates a breathability greater than about 100 $g/m^2/24$ hours and a load loss value at 50 percent elongation (on a total elongation of 70 percent) of less than about 50 percent.

In an alternative embodiment of the method, the filler is present in the blended elastomer composition between about 40 and 70 percent by weight. In still another alternative embodiment of the method, the elastomer in the blended elastomer composition is present between about 15 and 50 percent by weight. In still another alternative embodiment of the method, the semi-crystalline polymer is a polyethylene or polyethylene copolymer and has a melt index greater than about 5 g/10 min. In still another alternative embodiment of the method, the semi-crystalline polymer is a polyethylene or polyethylene copolymer and has a melt index greater than about 10 g/10 min. In still another alternative embodiment of the method, the semi-crystalline polymer has a density of greater than about 0.910 g/cc. In still another alternative embodiment of the method, the semi-crystalline polymer has a density of greater than about 0.915 g/cc. In still another alternative embodiment of the method, the semi-crystalline polymer has a density of about 0.917 g/cc. In still another alternative embodiment of the method, the semi-crystalline polymer has a density of between about 0.917 g/cc and 0.923 g/cc. In still another alternative embodiment of the method, the semi-crystalline polymer has a density of beween about 0.923 g/cc and 0.960 g/cc. In still another alternative embodiment of the method, the semi-crystalline polymer has a density of between about 0.917 g/cc and 0.960 g/cc. In still another alternative embodiment of the method, the semi-crystalline polymer is a polypropylene or polypropylene copolymer having a MFR greater than about 10 g/10 min. and a density between about 0.89 g/cc and 0.90 g/cc.

In a further alternative embodiment of the method, the filled polymer contains between about 60 and 85 percent by weight filler. In still a further alternative embodiment of the method, the filled polymer contains greater than about 75 percent by weight filler. In still a further alternative embodiment of the method, the filled polymer contains greater than about 80 percent by weight filler. In still a further alternative embodiment of the method, the blended elastomer composition contains between about 45 and 65 percent filler by weight. In still a further alternative embodiment of the method, the blended elastomer composition contains between about 5 and 25 percent by weight semi-crystalline polymer. In yet another alternative embodiment of the method, the blended elastomer composition contains between about 10 and 25 percent by weight semi-crystalline polymer. In yet another alternative embodiment of the method, the blended elastomer composition contains between about 20 and 50 percent thermoplastic elastomer. In still another alternative embodiment of the method, the blended elastomer composition contains between about 20 and 40 percent thermoplastic elastomer. In still another alternative embodiment of the method, the method includes the further step of orienting the film in the cross-machine direction.

An elastic, breathable film includes a thermoplastic elastomer and a filled semi crystalline predominantly linear polymer. The film includes between about 25 and 70 weight percent filler, between about 5 and 30 by weight percent semi-crystalline linear polymer, and between about 15 and 60 by weight of the elastomer, wherein the filler is closely associated with the semi-crystalline linear polymer, and further wherein the film demonstrates a load loss value at a 50 percent elongation (on a total elongation of 70 percent) of less than 50 percent, and a breathability of greater than 100 g/m$^2$/24 hours. In an alternative embodiment of the elastic, breathable film, the semi-crystalline polymer is a polyethylene or polyethylene copolymer and has a melt index greater than about 5 g/10 min. In yet another alternative embodiment of the elastic, breathable film, the semi-crystalline polymer is a polyethylene or polyethylene copolymer and has a melt index greater than about 10 g/10 min. In yet another alternative embodiment of the elastic, breathable film, the semi-crystalline polymer has a density of greater than about 0.910 g/cc (cm$^3$). In yet another alternative embodiment of the elastic, breathable film, the semi-crystalline polymer has a density of greater than about 0.915 g/cc. In yet another alternative embodiment of the elastic, breathable film, the semi-crystalline polymer has a density of about 0.917 g/cc. In yet another alternative embodiment of the elastic, breathable film, the semi-crystalline polymer has a density of between about 0.917 g/cc and 0.923 g/cc. In yet another alternative embodiment of the elastic, breathable film, the semi-crystalline polymer has a density of between about 0.923 g/cc and 0.960 g/cc. In yet another alternative embodiment of the elastic, breathable film, the semi-crystalline polymer has a density of between about 0.917 g/cc and 0.960 g/cc. In yet another alternative embodiment of the elastic, breathable film, the semi-crystalline polymer is a polypropylene or polypropylene copolymer having a MFR greater than about 10 g/10 min. and a density between about 0.89 g/cc and 0.90 g/cc. In yet another alternative embodiment of the elastic, breathable film, the film demonstrates a percent set of less than about 50 percent. In yet another alternative embodiment of the elastic, breathable film, the film demonstrates a percent set of between about 20 and 50 percent. In yet another alternative embodiment of the elastic, breathable film, the film demonstrates a percent set of less than about 20 percent. In yet another alternative embodiment of the elastic, breathable film, the film demonstrates a load loss of less than about 45 percent. In yet another alternative embodiment of the elastic, breathable film, the film demonstrates a load loss of less than about 35 percent. In yet another alternative embodiment of the elastic, breathable film, the elastomer is a styrenic block copolymer. In yet another alternative embodiment of the elastic, breathable film, the breathability is greater than about 1,000 g/m$^2$/24 hours. In yet another alternative embodiment of the elastic, breathable film, the filler is present in the blended elastomer composition between about 40 and 70 weight percent. In yet another alternative embodiment of the elastic, breathable film, the filler is present in the blended elastomer composition between about 45 and 65 weight percent. In yet another alternative embodiment of the elastic, breathable film, the elastomer is present between about 15 and 50 percent by weight. In yet another alternative embodiment of the elastic, breathable film, the elastomer is present between about 20 and 50 weight percent. In yet another alternative embodiment of the elastic, breathable film, the semi-crystalline polymer is present between about 5 and 25 weight percent. In yet another alternative embodiment of the elastic, breathable film, the semi-crystalline polymer is present between about 10 and 25 weight percent.

BRIEF DESCRIPTION OF THE DRAWINGS

The invention will be better understood by reference to the following description of embodiments of the invention taken in conjunction with the accompanying drawings, wherein.

DETAILED DESCRIPTION OF THE INVENTION

Figure 1:
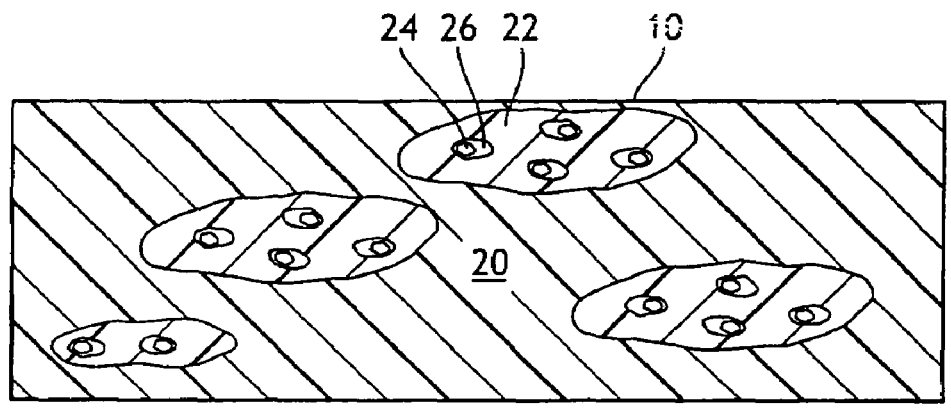
FIG. 1 is a cross sectional view of a film made in accordance with the invention.

Definitions:

As used herein, the term "personal care product" means diapers, training pants, swimwear, absorbent underpants, adult incontinence products, and feminine hygiene products, such as feminine care pads, napkins and pantiliners.

As used herein the term "protective outer wear" means garments used for protection in the workplace, such as surgical gowns, hospital gowns, masks, and protective coveralls.

As used herein, the term "protective cover" means covers that are used to protect objects such as for example car, boat and barbeque grill covers, as well as agricultural fabrics.

As used herein the terms "polymer" and "polymeric" generally include but are not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, the terms "machine direction" or MD means the length of a fabric in the direction in which it is produced. The terms "cross machine direction," "cross directional," or CD mean the width of fabric, i.e. a direction generally perpendicular to the MD.

As used herein, the term "nonwoven web" means a polymeric web having a structure of individual fibers or threads which are interlaid, but not in an identifiable, repeating manner. Nonwoven webs have been, in the past, formed by a variety of processes such as, for example, meltblowing processes, spunbonding processes, hydroentangling, air-laid and bonded carded web processes.

As used herein, the term "bonded carded webs" refers to webs that are made from staple fibers which are usually purchased in bales. The bales are placed in a fiberizing unit/picker which opens the bale from the compact state and separates the fibers. Next, the fibers are sent through a combining or carding unit which further breaks apart and aligns the staple fibers in the machine direction so as to form a machine direction-oriented fibrous non-woven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern through the web and or alternatively the web may be bonded across its entire surface if so desired. When using bicomponent staple fibers, through-air bonding equipment is, for many applications, especially advantageous.

As used herein the term "spunbond" refers to small diameter fibers which are formed by extruding molten thermoplastic material as filaments from a plurality of fine, usually circular capillaries of a spinneret with the diameter of the extruded filaments being rapidly reduced as by for example in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,542,615 to Dobo et al., which are each incorporated by reference in their entirety herein.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al.

As used herein the term "sheet" or "sheet material" refers to woven materials, nonwoven webs, polymeric films, polymeric scrim-like materials, and polymeric foam sheeting.

The basis weight of nonwoven fabrics is usually expressed in ounces of material per square yard (osy) or grams per square meter ($g/m^2$ or gsm) and the fiber diameters useful are usually expressed in microns. (Note that to convert from osy to gsm, multiply osy by 33.91). Film thicknesses may also be expressed in microns.

As used herein the term "laminate" refers to a composite structure of two or more sheet material layers that have been adhered through a bonding step, such as through adhesive bonding, thermal bonding, point bonding, pressure bonding, extrusion coating or ultrasonic bonding.

As used herein, the term "elastomeric" shall be interchangeable with the term "elastic" and refers to sheet material which, upon application of a stretching force, is stretchable in at least one direction (such as the CD direction), and which upon release of the stretching force contracts/returns to approximately its original dimension. For example, a stretched material having a stretched length which is at least 50 percent greater than its relaxed unstretched length, and which will recover to within at least 50 percent of its stretched length upon release of the stretching force. A hypothetical example would be a one (1) inch sample of a material which is stretchable to at least 1.50 inches and which, upon release of the stretching force, will recover to a length of not more than 1.25 inches. Desirably, such elastomeric sheet contracts or recovers up to 50 percent of the stretch length in the cross machine direction using a cycle test as described herein to determine percent set. Even more desirably, such elastomeric sheet material recovers up to 80 percent of the stretch length in the cross machine direction using a cycle test as described. Even more desirably, such elastomeric sheet material recovers greater than 80 percent of the stretch length in the cross direction using a cycle test as described. Desirably, such elastomeric sheet is stretchable and recoverable in both the MD and CD directions. For the purposes of this application, values of load loss and other "elastomeric functionality testing" have been generally measured in the CD direction, unless otherwise noted. Unless otherwise noted, such test values have been measured at 50 percent elongation on a 70 percent total elongation cycle (as described further in the test method section).

As used herein, the term "elastomer" shall refer to a polymer which is elastomeric.

As used herein, the term "thermoplastic" shall refer to a polymer which is capable of being melt processed.

As used herein, the term "inelastic" or "nonelastic" refers to any material which does not fall within the definition of "elastic" above.

As used herein, the term "breathable" refers to a material which is permeable to water vapor. The water vapor transmission rate (WVTR) or moisture vapor transfer rate (MVTR) is measured in grams per square meter per 24 hours, and shall be considered equivalent indicators of breathability. The term "breathable" desirably refers to a material which is permeable to water vapor having a minimum WVTR (water vapor transmission rate) of desirably about 100 g/m$^2$/24 hours. Even more desirably, such material demonstrates breathability greater than about 300 g/m$^2$/24 hours. Still even more desirably, such material demonstrates breathability greater than about 1000 g/m$^2$/24 hours.

The WVTR of a fabric, in one aspect, gives an indication of how comfortable a fabric would be to wear. WVTR is measured as indicated below. Often, personal care product applications of breathable barriers desirably have higher WVTRs and breathable barriers of the present invention can have WVTRs exceeding about 1,200 g/m$^2$/24 hours, 1,500 g/m$^2$/24 hours, 1,800 g/m$^2$/24 hours or even exceeding 2,000 g/m$^2$/24 hours.

As used herein, the term "multilayer laminate" means a laminate including a variety of different sheet materials. For instance, a multi-layered laminate may include some layers of spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al., and U.S. Pat. No. 5,188,885 to Timmons et al., each incorporated by reference in their entirety. Such a laminate may be made by sequentially depositing onto a moving forming belt first a spunbond fabric layer, then a meltblown fabric layer and last another spunbond layer and then bonding the laminate. Alternatively, the fabric layers may be made individually, collected in rolls, and combined in a separate bonding step or steps. Multilayer laminates may also have various numbers of meltblown layers or multiple spunbond layers in many different configurations and may include other materials like films or coform materials, e.g. SMMS, SM and SFS.

As used herein, the term "coform" means a process in which at least one meltblown diehead is arranged near a chute through which other materials are added to the web while it is forming. Such other materials may be pulp, superabsorbent particles, cellulosic fibers or staple fibers, for example. Corform processes are shown in commonly assigned U.S. Pat. No. 4,818,464 to Lau and U.S. Pat. No. 4,100,324 to Anderson et al., each incorporated by reference in their entirety.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen pattern having a bond area in the range of from about 15% to about 21% and about 302 bonds per square inch. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger, incorporated by reference herein in its entirety.

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein and in the claims, the term "comprising" is inclusive or open-ended and does not exclude additional unrecited elements, compositional components, or method steps. Accordingly, such terms are intended to be synonymous with the words "has", "have", "having", "includes", "including", and any derivatives of these words.

As used herein the terms "recover", "recovery" and "recovered" shall be used interchangeably and shall refer to a contraction of a stretched material upon termination of a stretching force following stretching of the material by application of the stretching force. For example, if a material having a relaxed, unstretched length of 1 inch (2.5 cm) is elongated fifty percent by stretching to a length of 1.5 inches (3.75 cm), the material would be elongated 50 percent and would have a stretched length that is 150 percent of its relaxed length or stretched 1.5×. If this exemplary stretched material contracted, that is recovered to a length of 1.1 inches (2.75 cm) after release of the stretching force, the material would have recovered 80 percent of its 0.5 inch (1.25 cm) elongation. Percent recovery may be expressed as [(maximum stretch length−final sample length)/(maximum stretch length−initial sample length)]×100.

As used herein the term "extensible" means elongatable in at least one direction, but not necessarily recoverable.

As used herein the term "percent stretch" refers to the ratio determined by measuring the increase in the stretched dimension and dividing that value by the original dimension. i.e. (increase in stretched dimension/original dimension)×100.

As used herein the term "set" refers to retained elongation in a material sample following the elongation and recovery, i.e. after the material has been stretched and allowed to relax during a cycle test.

As used herein the term "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set.

The "load loss" value is determined by first elongating a sample to a defined elongation in a particular direction (such as the CD) of a given percentage (such as 70 or 100 percent as indicated) and then allowing the sample to retract to an amount where the amount of resistance is zero. The cycle is repeated a second time and the load loss is calculated at a given elongation, such as at the 50 percent elongation. Unless otherwise indicated, the value was read at the 50% elongation level (on a 70 percent elongation test) and then used in the calculation. For the purposes of this application, the load loss was calculated as follows:

cycle 1 extension tension (at 50% elongation)−cycle 2 retraction tension (at 50% elongation)×100
cycle 1 extension tension (at 50% elongation)

For the test results reflected in this application, the defined elongation was 70 percent unless otherwise noted. The actual test method for determining load loss values is described below.

As used herein, a "filler" is meant to include particulates and/or other forms of materials which can be added to a film polymer extrusion material which will not chemically interfere with or adversely affect the extruded film and further which are capable of being dispersed throughout the film. Generally the fillers will be in particulate form with average particle sizes in the range of about 0.1 to about 10 microns, desirably from about 0.1 to about 4 microns. As used herein, the term "particle size" describes the largest dimension or length of the filler particle.

As used herein the terms semi-crystalline, predominantly linear polymer and semi-crystalline polymer shall refer to polyethylene, polypropylene, blends of such polymers and copolymers of such polymers. For such polyethylene-based polymers, such term shall be defined to mean polymers having a melt index of greater than about 5 g/10 min, but desirably greater than 10 g/10 min (Condition E at 190° C., 2.16 kg) and a density of greater than about 0.910 g/cc, but desirably greater than about 0.915 g/cc. In one embodiment, the density is between about 0.915 g/cc and 0.960 g/cc. In a further alternative embodiment, the density is about 0.917 g/cc. In a further alternative embodiment, the density is between about 0.917 g/cc and 0.960 g/cc. In still a further alternative embodiment, the density is between about 0.917 g/cc and 0.923 g/cc. In still a further alternative embodiment, the density is between about 0.923 g/cc and 0.960 g/cc. For such polypropylene based polymers, such term shall be defined to mean polymers having a melt flow rate greater than about 10 g/10 min, but desirably greater than about 20 g/10 min. (230° C., 2.16 kg ) and having a density between about 0.89 g/cc and 0.90 g/cc.

Unless otherwise indicated, percentages of components in formulations are by weight.

Test Method Procedures:

Water Vapor Transmission Rate (WVTR)/Breathability:

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. This information is used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F p_{sat}(T) RH / (A p_{sat}(T)(1-RH))$$

where:
F=The flow of water vapor in cc/min.,
$p_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

For the purposes of this Application, the testing temperature for the above test was at about 37.8° C., the flow was at 100 cc/min, and the relative humidity was at 60%. Additionally, the value for n was equal to 6 and the number of cycles was 3.

Cycle Testing:

The materials were tested using a cyclical testing procedure to determine load loss and percent set. In particular 2 cycle testing was utilized to 70 percent defined elongation. For this test, the sample size was 3 inch in the MD by 6 inch in the CD. The Grip size was 3 inch width. The grip separation was 4 inch. The samples were loaded such that the cross-direction of the sample was in the vertical direction. A preload of approximately 10–15 grams was set. The test pulled the sample at 20 inches/min (500 mm/min) to 70 percent elongation (2.8 inches in addition to the 4 inch gap), and then immediately (without pause) returned to the zero point (the 4 inch gauge separation). In-process testing (resulting in the data in this application) was done as a 2 cycle test. The results of the test data are all from the first and second cycles. The testing was done on a Sintech Corp. constant rate of extension tester 2/S with a Renew MTS mongoose box (controller) using TESTWORKS 4.07 b software. (Sintech Corp, of Cary, N.C.). The tests were conducted under ambient conditions.

Melt Index or Melt Flow Rate

Melt Index (MI) or Melt Flow Rate (MFR) depending on the polymer being tested, is a measure of how easily a resin flows at a given temperature and shear rate, and can be determined using ASTM Standard D1238, condition 190° C./2.16 kg (Condition E) generally for polyethylene-based polymers. The melt index test data in this application were produced in accordance with this method and condition. In general, a polymer having a high melt index has a low viscosity. For polypropylene-based polymers, a similar analysis is conducted for melt flow rate at a condition of 230° C. and 2.16 kg. In accordance with the present invention the combination of melt index or melt flow rate (depending on polymer) and density parameters of the carrier resin results in the improved two phase film with increased ability for the carrier resin to aid in processing and to retain pore formation following stretching. In particular, it has been determined that non-elastic, more crystalline carrier resins with higher MI values (above about 5 g/10 min) and density values (between about 0.910 g/cc and 0.960 g/cc for polyethylene-based polymers) were particularly effective at producing breathable films without sacrificing elastic performance. In particular, carrier resins with densities greater than about 0.915 g/cc are desirable. Such carrier resins with densities of about 0.917 g/cc are also desirable. Such carrier resins with densities greater than about 0.917 g/cc are also desirable. In still a further embodiment, such carrier resins with densities between 0.917 g/cc and 0.960 g/cc are desirable. In still a further alternative embodiment, such carrier resins with densities between about 0.917 g/cc and 0.923 g/cc are also desirable. In still a further alternative embodiment, such carrier resins with densities between about 0.923 g/cc and 0.960 g/cc are also desirable. In an alternative embodiment, polypropylene-based carrier resins with lower densities such as about 0.89 g/cc, would also be useful, especially those with a MFR of greater than about 10 g/10 min, but desirably 20 g/10 min MFR or greater (conditions 230° C., 2.16 kg). In still a further alternative embodiment, such polypropylene-based carrier resins with densities between about 0.89 g/cc and 0.90 g/cc can also be utilized. It is also desirable to blend such carrier resins separately with a filler, prior to blending the carrier/filler mixture with the elastomer component, so that all materials are not compounded together in a single step. It is desirable that the filler be maintained in close association with the carrier rather than blending any filler directly with the elastomer component, such that the carrier resin forms filler rich pockets within the elastomer component.

The present invention intends to overcome the above problems of prior art elastic films. The problems are addressed by a filled film wherein the film composition provides breathability and elasticity without pore collapse. Further advantages, features, aspects and details of the invention are evident from the claims, the description and the accompanying drawings.

Two methods of formulating films for making breathable filled films are a concentrate letdown approach and a fully compounded approach. For the purposes of the films of the current application, the concentrate letdown approach is desirable. In the concentrate letdown process, one resin is used as a carrier resin to make a concentrate with a filler. In the current application, the carrier resin, typically a high melt index or melt flow rate/low viscosity resin with higher density level for polyethylene-based polymers (0.910 g/cc–0.960 g/cc), and a density level between about 0.89 g/cc and 0.90 g/cc for polypropylene-based polymers, is used to disperse high loadings of filler. The elastic letdown resin dominates the elastic properties of the film. The concentrate is let down (combined) with elastic resin to dilute the final filler content to a desired percentage.

The elastic, thermoplastic filled breathable film of the present invention is made from a thermoplastic elastomer let down resin, desirably a block copolymer (such as a styrenic block copolymer) that has been blended with a semi-crystalline, predominantly linear polymer (carrier resin) which includes a filler (the "concentrate"). Desirably, the elastic polymer is blended with a single screw extruder so as to avoid/reduce substantial mixing of the polymer phases, and retain pockets of the carrier resin within the letdown resin. The filler, such as calcium carbonate, creates filled regions within the extruded film, that can be stretched to form pores at the semi-crystalline polymer/filler interface, without negatively impacting the elastic recovery of the non-filled elastic polymer component. It is theorized that the pores in the filled regions do not collapse as the formed pores are surrounded by an inelastic semi-crystalline polymer shell.

As was stated previously, either higher density polyethylene-based carrier resins or polypropylene-based carrier resins with densities between 0.89 g/cc and 0.90 g/cc are preferred. Desirably, the filled carrier semi-crystalline polymer (filled polymer or concentrate) is compounded with the filler prior to combining with the thermoplastic elastomer let down resin to surround the filler particle only with the semi crystalline polymer, thus forming a predominantly non-elastic shell around the filler particles, capable of pore formation and retention when the film of this composition is stretched.

As can be seen in FIG. 1, which illustrates a cross sectional view of a film (product film that has been stretched) made in accordance with the invention, the film 10 includes an elastomeric component 20. Semi-crystalline polymer/filler rich pockets 22 are dispersed throughout the elastomeric component, desirably with the filler isolated to the carrier resin locations. Filler particles 24 are contained within the semi-crystalline polymer pockets or pores. The pores are created by the hard shell/walls of the semi-crystalline polymer phase within the elastomeric polymer phase. The pores/spaces 26 are formed between the semi-crystalline polymers and the filler particles as the film is stretched in a machine direction orienter or other stretching device. Since the shells are made of a semi-crystalline material, they retain much of their shape, albeit in a compressed or elongated oval-type shape when stretched uniaxially, rather than a perfectly circular configuration. The shells retain a more circular configuration when stretched biaxially. It should be recognized that the illustration of FIG. 1 is a stylized schematic image.

Various thermoplastic elastomers are contemplated for use in this invention. However, thermoplastic block polymers such as styrenic block copolymers are examples of useful elastic polymers of the invention. Specific examples of useful styrenic block copolymers include hydrogenated polyisoprene polymers such as styrene-ethylenepropylene-styrene (SEPS), styrene-ethylenepropylene-styrene-ethylenepropylene (SEPSEP), hydrogenated polybutadiene polymers such as styrene-ethylenebutylene-styrene (SEBS), styrene-ethylenebutylene-styrene-ethylenebutylene (SEBSEB), styrene-butadiene-styrene (SBS), styrene-isoprene-styrene (SIS), and hydrogenated poly-isoprene/butadiene polymer such as styrene-ethylene-ethylenepropylene-styrene (SEEPS). Polymer block configurations such as diblock, triblock, multiblock, star and radial are also contemplated in this invention. In some instances, higher molecular weight block copolymers may be desirable. Block copolymers are available from Kraton Polymers U.S. LLC of Houston, Tex. under the designations Kraton D or G polymers, for example G1652 and G1657 and Septon Company of America, Pasadena, Tex. under the designations Septon 2004, Septon 4030, and Septon 4033. Another potential supplier of such polymers includes Dynasol of Spain. In particular, Septon 2004 SEPS triblock polymer is particularly suitable for the invention. Blends of such elastomeric materials are also contemplated as the "elastomeric component". For instance, a blend of G1652 and G1657 may be utilized, such that an elastomeric component may be present in a final film formulation at about 33% by weight, 10 percent (of the total film formula) of which is G1652 and 23 percent (of the total film formula) of which is G1657. Such an embodiment could include filler and concentrate as the remaining 67 percent by weight. In one embodiment, it is desirable that the styrenic block copolymer is a SEPS polymer. The thermoplastic elastomers themselves may include processing aids and/or tackifiers associated with the elastomeric polymers. Other thermoplastic elastomers useful in the invention include olefinic-based elastomers such as EP rubber, ethyl, propyl, butyl terpolymers, block and copolymers thereof.

Desirably, the film of the filler, carrier resin and elastomeric letdown resin materials includes between about 15 and 50 weight percent elastomeric polymer component. More desirably, the product film of the blended materials includes between about 20 and 40 weight percent elastomer. It should be recognized, that when the elastomer component of the blended elastomeric composition is given, it may include neat base resins along with processing aids such as low molecular weight hydrocarbon materials such as waxes, amorphous polyolefins and/or tackifiers.

Both organic and inorganic fillers are contemplated for use with the present invention, provided they do not interfere with the film forming process and/or subsequent laminating processes. Examples of fillers include calcium carbonate ($CaCO_3$), various clays, silica ($SiO_2$), alumina, barium sulfate, sodium carbonate, talc, magnesium sulfate, titanium dioxide, zeolites, aluminum sulfate, cellulose-type powders, diatomaceous earth, gypsum, magnesium sulfate, magnesium carbonate, barium carbonate, kaolin, mica, carbon, calcium oxide, magnesium oxide, aluminum hydroxide, pulp powder, wood powder, cellulose derivatives, polymeric particles, chitin and chitin derivatives.

The filler particles may optionally be coated with a fatty acid, such as stearic acid or behenic acid, and/or other material in order to facilitate the free flow of the particles (in bulk) and their ease of dispersion into the carrier polymer. One such filler is calcium carbonate sold under the brand Supercoat®, of Imerys of Roswell, Ga. Another is Omyacarb® 2 SS T of Omya, Inc. North America of Proctor, Vt. The later filler is coated with stearic acid. Desirably, the amount of filler in the product film (final film formulation) is between about 40 and 70 weight percent. More desirably, the amount of filler in the product film is between about 45 and 60 weight percent.

Examples of semi-crystalline carrier polymers useful in compounding with filler include, but are not limited to predominantly linear polyolefins (such as polypropylene and polyethylene) and copolymers thereof. Such carrier materials are available from numerous sources. Specific examples of such semi-crystalline polymers include ExxonMobil 3155, Dow polyethylenes such as Dowlex 2517 (25 MI, 0.917 g/cc); Dow LLDPE DNDA-1082 (155 MI, 0.933 g/cc), Dow LLDPE DNDB-1077 (100 MI, 0.929 g/cc), Dow LLDPE 1081 (125 MI, 0.931 g/cc), and Dow LLDPE DNDA 7147 (50 MI, 0.926 g/cc). In some instances, higher density polymers may be useful, such as Dow HDPE DMDA-8980 (80 MI, 0.952 g/cc). Additional resins include Escorene LL 5100, having a MI of 20 and a density of 0.925 and Escorene LL 6201, having a MI of 50 and a density of 0.926 from ExxonMobil In an alternative embodiment, polypropylene carrier resins with lower densities such as at about 0.89 g/cc, would also be useful, especially those with a 10 g/10 min MFR, but desirably a 20 MFR or greater (conditions of 230° C., 2.16 kg). Polypropylen-based resins having a density of between 0.89 g/cc and 0.90 g/cc would be useful, such as homopolymers and random copolymers such as ExxonMobil PP3155 (36 MFR), PP1074KN (20 MFR), PP9074MED (24 MFR) and Dow 6D43 (35 MFR).

It is desirable that the melt index of the semi-crystalline polymer (for polyethylene-based polymers) be greater than about 5 g/10 min, as measured by ASTM D1238 (2.16 kg, 190° C.). More desirably, the melt index of the semi-crystalline polymer is greater than about 10 g/10 min. Even more desirably, the melt index is greater than about 20 g/10 min. Desirably, the semi-crystalline carrier polymer has a density of greater than about 0.910 g/cc, but even more desirably greater than about 0.915 g/cc for polyethylene-based polymers. Even more desirably, the density is about 0.917 g/cc. In another alternative embodiment, the density is greater than 0.917 g/cc In still another alternative embodiment, the density is between about 0.917 g/cc and 0.923 g/cc. In still another alternative embodiment, the semi-crystalline carrier polymer has a density between about 0.917 and 0.960 g/cc. In yet another alternative embodiment, the semi-crystalline polymer has a density between about 0.923 g/cc and 0.960 g/cc. It is also desirable that the film contains between about 10 and 25 weight percent semi-crystalline polymer.

In addition, the breathable filled film may optionally include one or more stabilizers or processing aids. For instance, the filled-film may include an anti-oxidant such as, for example, a hindered phenol stabilizer. Commercially available anti-oxidants include, but are not limited to, IRGANOX™ E 17 (a-tocopherol) and IRGANOX™ 1076 (octodecyl 3,5-di-tert-butyl-4-hydroxyhydrocinnamate) which are available from Ciba Specialty Chemicals of Tarrytown, N.Y. In addition, other stabilizers or additives which are compatible with the film forming process, stretching and any subsequent lamination steps, may also be employed with the present invention. For example, additional additives may be added to impart desired characteristics to the film such as, for example, melt stabilizers, processing stabilizers, heat stabilizers, light stabilizers, heat aging stabilizers and other additives known to those skilled in the art. Generally, phosphite stabilizers (i.e. IRGAFOS 168 available from Ciba Specialty Chemicals of Tarrytown, N.Y. and DOVERPHOS available from Dover Chemical Corp. of Dover, Ohio) are good melt stabilizers whereas hindered amine stabilizers (i.e. CHIMASSORB 944 and 119 available from Ciba Specialty Chemicals of Tarrytown, N.Y.) are good heat and light stabilizers. Packages of one or more of the above stabilizers are commercially available such as B900 available from Ciba Specialty Chemicals. Desirably about 100 to 2000 ppm of the stabilizers are added to the base polymer(s) prior to extrusion (Parts per million is in reference to the entire weight of the filled-film).

Desirably, a concentrate of "filled polymer" (carrier resin and filler) is made with the filler and the semi-crystalline carrier polyolefin in the range of between about 60–85 percent by weight filler, but more desirably between about 70–85 percent by weight filler. It is also desirable to reduce the amount of the semi-crystalline polymer in the final composition so as to have the least impact on the elastic performance of the elastomeric polymer phase. The elastic polymer is blended with the filled polymer concentrate resin prior to introduction into the film screw extruder in a blending station as a "letdown" resin. The concentration of the block polymer is then generally determined by the desired filler level in the final composition. The level of filler will necessarily affect breathability as well as elastic properties of the film. In one embodiment it is desirable for the filler to be present in the filled polymer in an amount of greater than 80 weight percent, such that the film demonstrates the desired properties which are described below.

As an example, the filler may be present in a film configuration of between about 25–65 weight percent, the elastomer may be present in a range between about 15–60 weight percent, and the semi-crystalline polymer may be present in a range of between about 5–30 weight percent.

It is desirable for the purposes of this invention, to limit as much as possible the semi-crystalline polymer to the surface of the filler, so as not to fully compound the carrier resin polymer or filler throughout the elastic polymer blend, thereby limiting the mixing of the two polymers. The elastic polymer is then generally in a continuous phase throughout the film, maximizing the elastic performance.

In an alternative embodiment of the invention, the film can be laminated to one or more layers as part of a multi-layered laminate. For instance, the film can be laminated to one or more nonwoven or woven webs or scrims. In one embodiment, the film can be laminated to a spunbond web. Such spunbond web can be of a single component, or alternatively of a bicomponent/conjugate arrangement. Desirably, such spunbond web has a basis weight of between about 10 and 50 gsm. Alternatively, such film can be laminated to a coform, meltblown, or bonded carded web. The film may be laminated to additional sheet materials by adhesive, thermal calendaring, extrusion coating or ultrasonic bonding methods. In some instances, the layer that is laminated to the film may provide support to the film, and may be fairly characterized as a support layer. In other instances such additional layer may provide other types of functionality, such as an improved hand.

Figure 2:
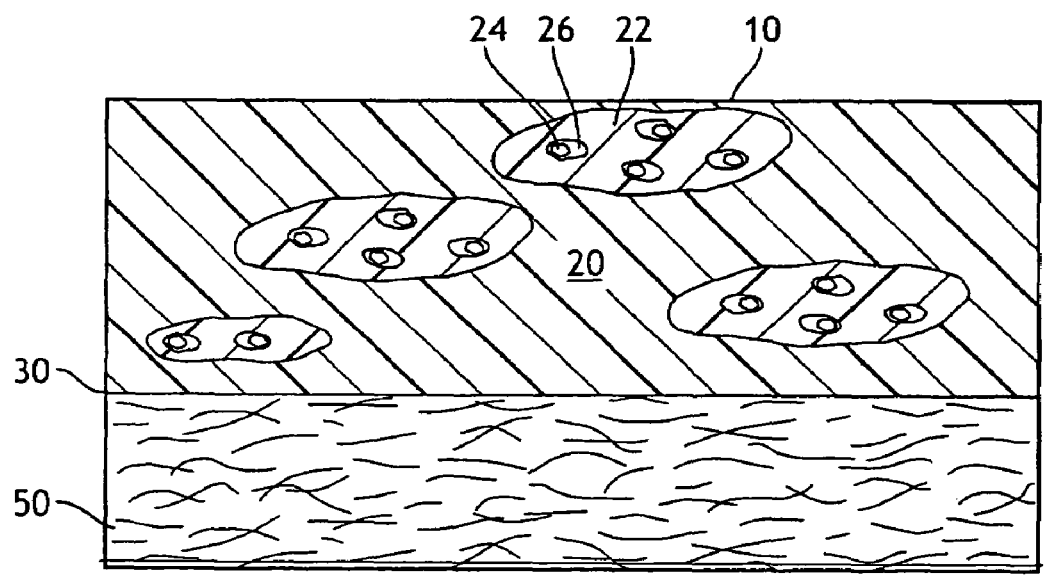
FIG. 2 is a cross-sectional view of a film/laminate made in accordance with the invention.

As can be seen in FIG. 2, a film laminate of the current invention is illustrated having a single layer breathable elastic film 10 and at least one additional attached support layer such as a nonwoven layer 50. Such nonwoven layer is attached by for instance an adhesive application 30.

Figure 3:
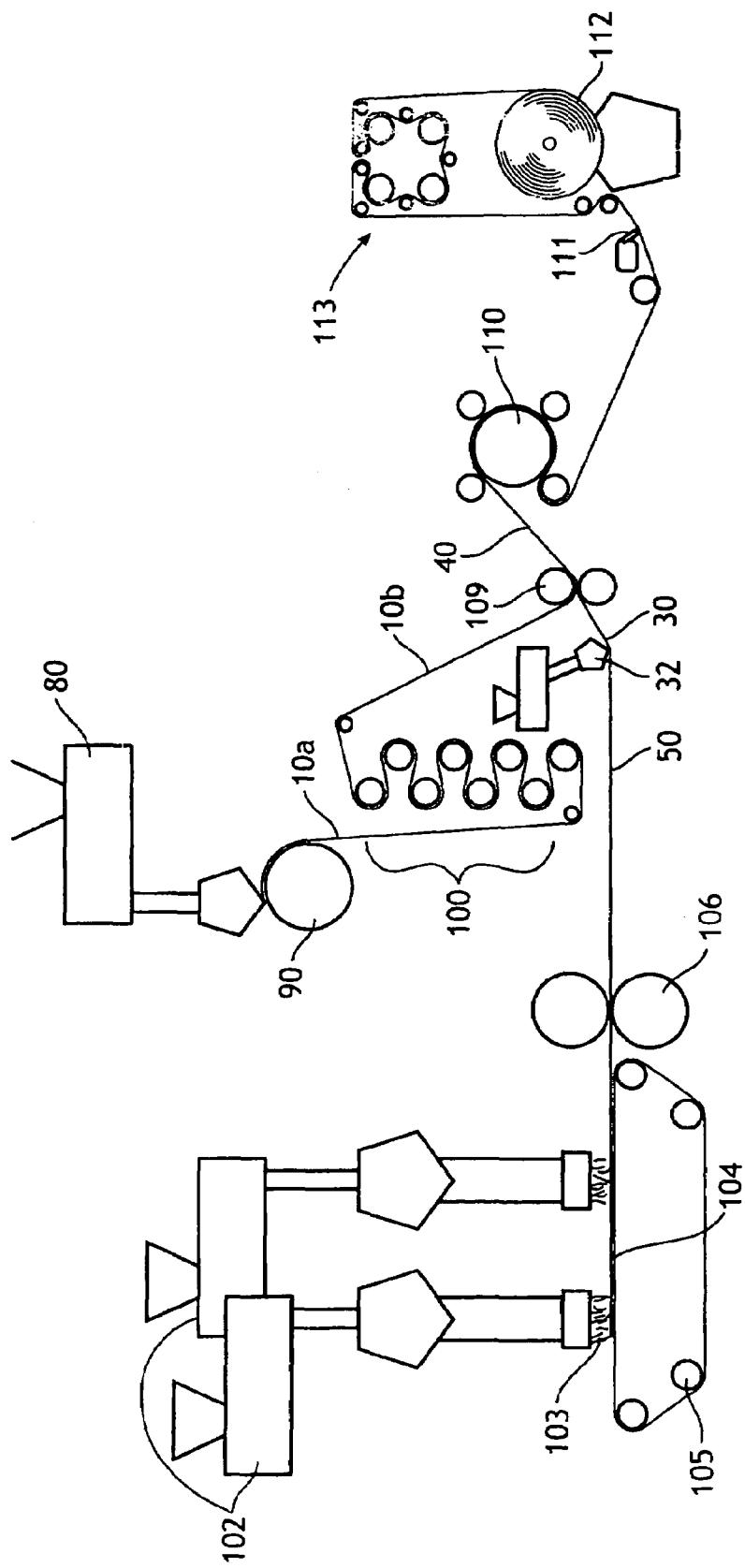
FIG. 3 is a schematic of a process used to make a film and laminate in accordance with the invention.

Process:

A process for forming the breathable, elastic film 10 is shown in FIG. 3 of the drawings. However, before the film is manufactured, the raw materials, i.e. the semi-crystalline carrier polymer(s) and filler must first be compounded such as through the following process. The filler and semi-crystalline polymer raw materials are added into a hopper of a twin screw extruder or high intensity mixer, (both available from Farrel Corporation, of Ansonia Conn.) and are dispersively mixed in the melt, by the action of the intermeshing rotating screws or rotors. The resulting mixture is pelletized and is referred to herein as the filler concentrate or filler concentrate compound. The filler concentrate compound and the elastomer resin are then desirably processed in a film process by means of a single, barrier screw extruder, followed by a melt pump feeding a film die. It should therefore be recognized that the materials are not all fully compounded together in one step, rather it is a separate step process that accomplishes the compounding of the carrier polymer with the filler and then another step which combines the filled carrier resin and the thermoplastic elastomer.

Referring again to the Figure, the compounded polymers and filler are placed in an extruder 80 apparatus and then cast or blown into a film. A precursor film 10a is then extruded (at a temperature range of between about 380–440° F., Examples in the range of 400–420° F.) onto for instance, a casting roll 90, which may be smooth or patterned. The term "precursor" film shall be used to refer to the film prior to being made breathable, such as by being run through a machine direction orienter. The flow out of the extruder die is immediately cooled on the casting roll 90. A vacuum box (not shown) may be situated adjacent the casting roll in order to create a vacuum along the surface of the roll to help maintain the precursor film 10a lying close to the surface of the roll. Additionally, air knives or electrostatic pinners (not shown) may assist in forcing the precursor film 10a to the casting roll surface as it moves around the spinning roll. An air knife is a device known in the art which focuses a stream of air at a very high flow rate to the edges of the extruded polymer material. The precursor film 10a (prior to run through the MDO) is desirably between about 20 and 100 microns in thickness, and has an overall basis weight of between about 30 gsm and 100 gsm. In one embodiment the basis weight is between about 50–75 gsm. Following stretching in a stretching apparatus, the basis weight of the film is between about 10 and 60 gsm, but desirably between about 15 and 60 gsm.

As previously stated, the precursor film 10a is subjected to further processing to make it breathable. Therefore, from the extrusion apparatus 80, and casting roll 90, the precursor film 10a is directed to a film stretching unit 100, such as a machine direction orienter or "MDO" which is a commercially available device from vendors such as the Marshall and Williams Company of Providence, R.I. This apparatus may have a plurality of stretching rollers (such as for example from 5 to 8) which progressively stretch and thin the film in the machine direction, which is the direction of travel of the film through the process as shown in FIG. 3. While the MDO is illustrated with eight rolls, it should be understood that the number of rolls may be higher or lower, depending on the level of stretch that is desired and the degrees of stretching between each roll. The film can be stretched in either single or multiple discrete stretching operations. It should be noted that some of the rolls in an MDO apparatus may not be operating at progressively higher speeds.

Desirably, the unstretched filled film 10a (precursor film) will be stretched (oriented) from about 2 to about 5 times its original length, imparting a final stretch of between 1.5 to about 4 times of the original film length after the film is allowed to relax at the winder. In an alternative embodiment, the film may be stretched through intermeshing grooved rolls such as those described in U.S. Pat. No. 4,153,751 to Schwarz.

Referring again to FIG. 3, some of the rolls of the MDO 100 may act as preheat rolls. If present, these first few rolls heat the film above room temperature (125° F.). The progressively faster speeds of adjacent rolls in the MDO act to stretch the filled precursor film 10a. The rate at which the stretch rolls rotate determines the amount of stretch in the film and final film weight. Microvoids are formed during this stretching to render the film microporous and subsequently breathable. After stretching, the stretched film 10b may be allowed to slightly retract and/or be further heated or annealed by one or more heated rolls 113, such as by heated anneal rolls. These rolls are typically heated to about 150–220° F. to anneal the film. The film may then be cooled. After exiting the MDO film stretching unit, the then breathable product film 10 may be wound on a winder for storage or proceed for further processing.

If desired, the produced product film 10 may be attached to one or more layers 50, such as nonwoven layers (for instance, spunbond), to form a multilayer film/laminate 40. Suitable laminate materials include nonwoven fabrics, multi-layered nonwoven fabrics or sheet materials, scrims, woven fabrics and other like materials. In order to achieve a laminate with improved body conformance, the fibrous layer is itself desirably an extensible fabric and even more desirably an elastic fabric. For example, tensioning a nonwoven fabric in the MD causes the fabric to "neck" or narrow in the CD and give the necked fabric CD extensibility. Examples of additional suitable extensible and/or elastic fabrics include, but are not limited to, those described in U.S. Pat. No. 4,443,513 to Meitner et al.; U.S. Pat. No. 5,116,662 to Morman et al.; U.S. Pat. No. 4,965,122 to Morman et al.; U.S. Pat. No. 5,336,545 to Morman et al.; U.S. Pat. No. 4,720,415 to Vander Wielen et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; and U.S. Pat. No. 5,540,976 to Shawver et al. The entire content of the aforesaid patents are incorporated herein by reference. Such necked nonwoven material may be bonded to the film of the present invention. In an alternative embodiment, a slit and necked nonwoven material may be bonded to the film of the present invention. In still a further alternative embodiment, a spunbond support layer may be stretched in grooved rolls from between 1.5 to 3× in the CD and then necked to the original width or to match the width of the film prior to being adhesively laminated to the film.

Nonwoven fabrics which may be laminated to such product films 10 desirably have a basis weight between about 10 g/m$^2$ and 50 g/m$^2$ and even more desirably between about 15 g/m$^2$ and 30 g/m$^2$. As a particular example, a 17 g/m$^2$ (0.5 ounces per square yard) web of polypropylene spunbond fibers can be necked a desired amount and thereafter laminated to a breathable stretched filled-product film 10. The product film 10 would therefore be nipped (in an adhesive nip, or lamination rolls of a calender roll assembly 109) to a necked or CD stretchable spunbond nonwoven web.

The spunbond layer, support layer, or other functional laminate layer may either be provided from a pre-formed roll, or alternatively, be manufactured in-line with the film and brought together shortly after manufacture. For instance, as is illustrated in FIG. 3, one or more spunbond extruders 102 meltspin spunbond fibers 103 onto a forming wire 104 that is part of a continuous belt arrangement. The continuous belt circulates around a series of rollers 105. A vaccum (not shown) may be utilized to maintain the fibers on the forming wire. The fibers may be compressed via compaction rolls 106. Following compaction, the spunbond or other nonwoven material layer is bonded to the product film 10. Such bonding may occur through adhesive bonding, such as through slot or spray adhesive systems, thermal bonding or other bonding means, such as ultrasonic, microwave, extrusion coating and/or compressive force or energy. An adhesive bonding system 32 is illustrated. Such a system may be a spray or a slot coat adhesive system. Examples of suitable adhesives that may be used in the practice of the invention include Rextac 2730, 2723 available from Huntsman Polymers of Houston, Tex., as well as adhesives available from Bostik Findley, Inc, of Wauwatosa, Wis. In an alternative embodiment, the film and nonwoven support layer are laminated with an adhesive such that the basis weight of the adhesive is between about 1.0 and 3.0 gsm. The type and basis weight of the adhesive used will be determined on the elastic attributes desired in the final laminate and end use. In another alternative embodiment, the adhesive is applied directly to the nonwoven support layer prior to lamination with the film. In order to achieve improved drape, the adhesive may be pattern applied to the outer fibrous layer.

The film and support layer material typically enter the lamination rolls at the same rate as the film exits the MDO. Alternatively, the film is tensioned or relaxed as it is laminated to the support layer. In an alternative embodiment, bonding agents or tackifiers may be added to the film to improve adhesion of the layers. As previously stated, the filled-film and fibrous layer can be adhesively laminated to one another. By applying the adhesive to the outer fibrous layer, such as a nonwoven fabric, the adhesive will generally only overlie the film at fiber contact points and thus provide a laminate with improved drape and/or breathability. Additional bonding aids or tackifiers can also be used in the fibrous or other outer layer.

After bonding, the laminate 40 may be further processed. Following lamination, the multilayered laminate may be subjected to numerous post-stretching manufacturing processes. For instance, such laminate may be slit, necked, apertured or printed. Alternatively, such laminate may be coursed through a series of grooved rolls that have grooves in either the CD or MD direction, or a combination of such. Such processing step 110 may provide additional desired attributes to the laminate 40, such as softness, without sacrificing elasticity or breathability. For instance, the grooved rolls may be constructed of steel or other hard material (such as a hard rubber) and may include between about 4 and 15 grooves per inch. In an alternative embodiment the grooved rolls may include between about 6 and 12 grooves per inch. In still a further alternative embodiment the grooved rolls include between about 8 and 10 grooves per inch. In still a further alternative embodiment grooves on such rolls include valleys of between about 100 thousandths and 25 thousandths of an inch. Following any additional treatment, the laminate may be further slit, 111, annealed 113, and/or wound on a winder 112.

The inventive film and/or film laminate may be incorporated into numerous personal care products. For instance, such materials may be particularly advantageous as a stretchable outer cover for various personal care products. Additionally, such film may be incorporated as a base fabric material in protective garments such as surgical or hospital drapes/gowns. In still a further alternative embodiment, such material may serve as a base fabric for protective recreational covers such as car covers and the like.

Figure 4:
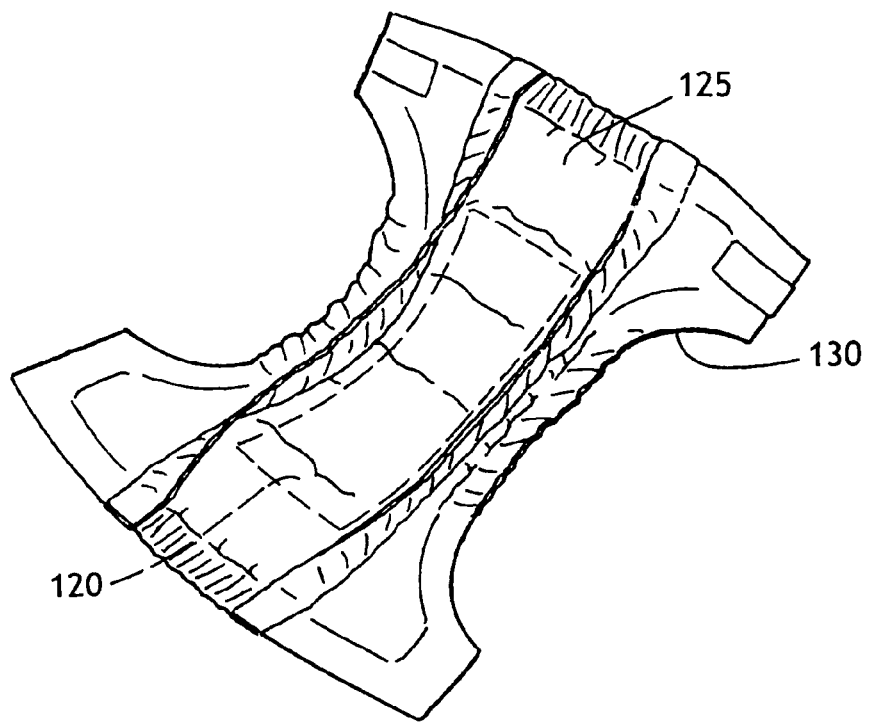
FIG. 4 is a drawing of a diaper made in accordance with the invention.

In this regard, FIG. 4 is a perspective view of an absorbent article, such as a disposable diaper of the present invention, in its opened state. The surface of the diaper which contacts the wearer is facing the viewer. With reference to FIG. 4, the disposable diaper generally defines a front waist section, a rear waist section, and an intermediate section which interconnects the front and rear waist sections. The front and rear waist sections include the general portions of the article which are constructed to extend substantially over the wearer's front and rear abdominal regions, respectively, during use. The intermediate section of the article includes the general portion of the article that is constructed to extend through the wearer's crotch region between the legs.

The absorbent article includes an outer cover 130, a liquid permeable bodyside liner 125 positioned in facing relation with the outer cover, and an absorbent body 120, such as an absorbent pad, which is located between the outer cover and the bodyside liner. The outer cover in the illustrated embodiment, coincide with the length and width of the diaper. The absorbent body generally defines a length and width that are less than the length and width of the outer cover, respectively. Thus, marginal portions of the diaper, such as marginal sections of the outer cover, may extend past the terminal edges of the absorbent body. In the illustrated embodiment, for example, the outer cover extends outwardly beyond the terminal marginal edges of the absorbent body to form side margins and end margins of the diaper. The bodyside liner is generally coextensive with the outer cover but may optionally cover an area which is larger or smaller than the area of the outer cover, as desired.

The outer cover and bodyside liner are intended to face the garment and body of the wearer, respectively, while in use. The film or film laminate of the present invention may conveniently serve as the outercover in such an article.

Fastening means, such as hook and loop fasteners, may be employed to secure the diaper on a wearer. Alternatively, other fastening means, such as buttons, pins, snaps, adhesive tape fasteners, cohesives, mushroom-and-loop fasteners, or the like, may be employed.

The diaper may also include a surge management layer located between the bodyside liner and the absorbent body to prevent pooling of the fluid exudates and further improve the distribution of the fluid exudates within the diaper. The diaper may further include a ventilation layer (not illustrated) located between the absorbent body and the outer cover to insulate the outer cover from the absorbent body to reduce the dampness of the garment facing surface of the outer cover.

The various components of the diaper are integrally assembled together employing various types of suitable attachment means, such as adhesive, sonic bonds, thermal bonds or combinations thereof. In the shown embodiment, for example, the bodyside liner and outercover may be assembled to each other and to the absorbent body with lines of adhesive, such as a hotmelt, pressure-sensitive adhesive. Similarly, other diaper components, such as elastic members and fastening members, and surge layer may be assembled into the article by employing the above-identified attachment mechanisms. The article of the invention desirably includes the distinctive film or film laminate as a stretchable fabric layer as part of a stretchable outer cover which is operatively attached or otherwise joined to extend over a major portion of the outward surface of the article. In regions where the stretchable outer cover is not affixed to non-stretchable portions of the article or otherwise restricted from extending, the stretchable outer cover can be free to advantageously expand with minimal force. In desired aspects, the outer cover can be stretchable along the longitudinal direction, lateral direction, or along a combination of both the lateral and longitudinal directions. In particular, it is desirable that at least the portion of the stretchable outer cover located in the waist sections be capable of extending in the lateral direction to provide improved fastening of the article about the wearers and improved coverage of the hips and buttocks of the wearer particularly in the rear waist section and enhanced breathability in the waist sections. For example, if the fasteners and or side panels are located along the side edges in the rear waist section of the diaper, at least a portion of the outer cover in the rear waist section will desirably extend to provide enhanced coverage over the buttocks of the wearer in use for improved containment and aesthetics. In a further alternative embodiment, the distinctive film of the invention may serve as a base material for stretchable ears/fastening tabs on the outer cover as well. In still another alternative embodiment of the present invention, the distinctive film may serve as the basis of a stretchable liner. In such an embodiment, the liner may be apertured. In still another alternative embodiment, the distinctive film may serve as a full stretchable outercover which encompasses both the front and rear areas of a personal care article, including stretchable side areas. This would eliminate the need to utilize distinct side panels in certain articles.

Moreover, it is also desirable that at least portions of the stretchable outer cover located over the absorbent body can extend during use for improved containment. For example, as the absorbent body absorbs fluid exudates and expands outwardly, the stretchable outer cover can readily elongate and extend in correspondence with the expansion of the absorbent body and/or other components of the article to provide void volume to more effectively contain the exudates. The stretchable outer cover of the present invention is desirably capable of providing a selected stretch when subjected to an applied tensile force, and the ability to retract upon removal of such applied force.

Figure 5:
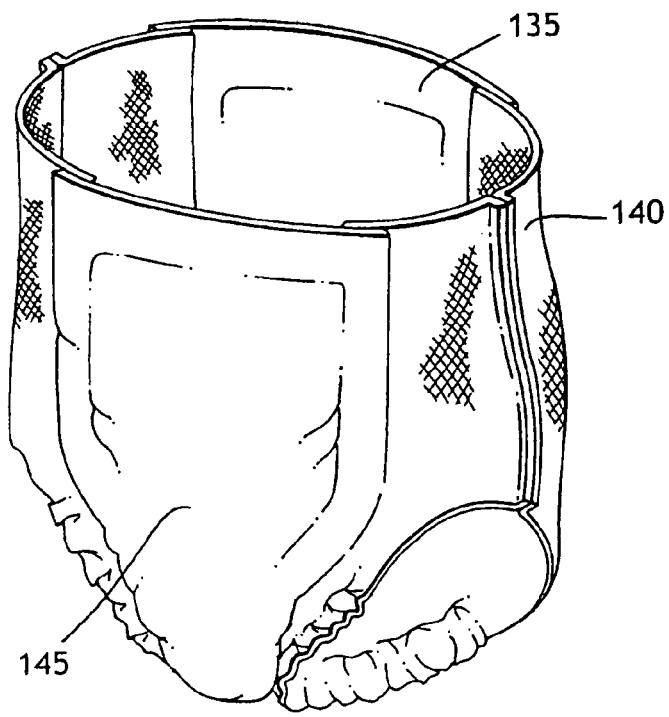
FIG. 5 is a drawing of a training pant made in accordance with the invention.
Figure 6:
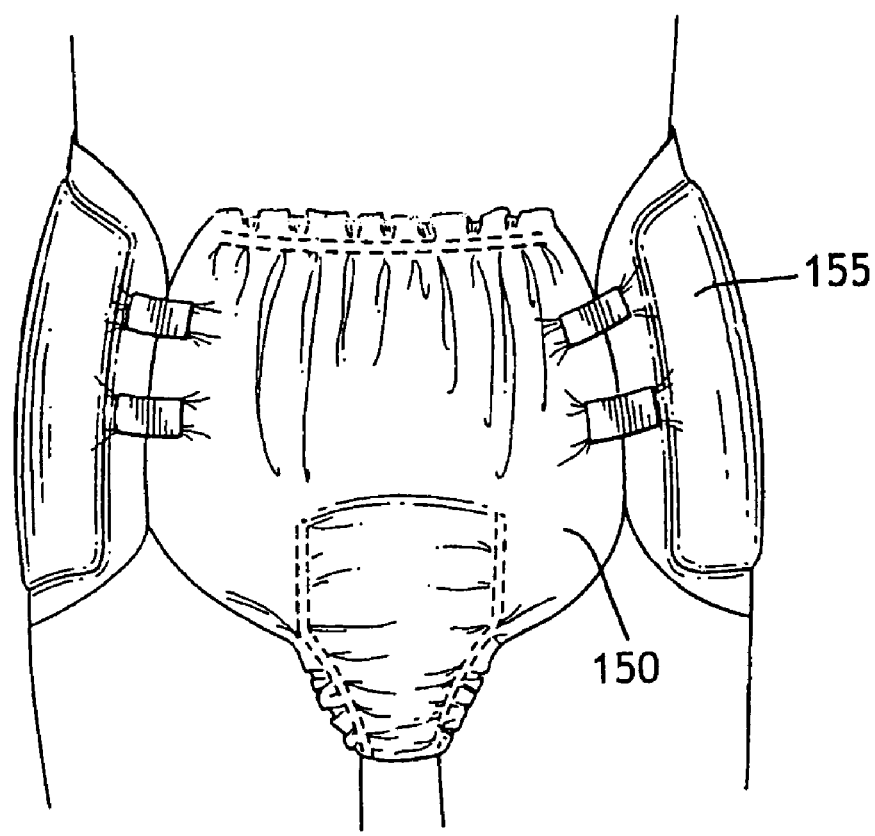
FIG. 6 is a drawing of an absorbent underpant made in accordance with the invention
Figure 7:
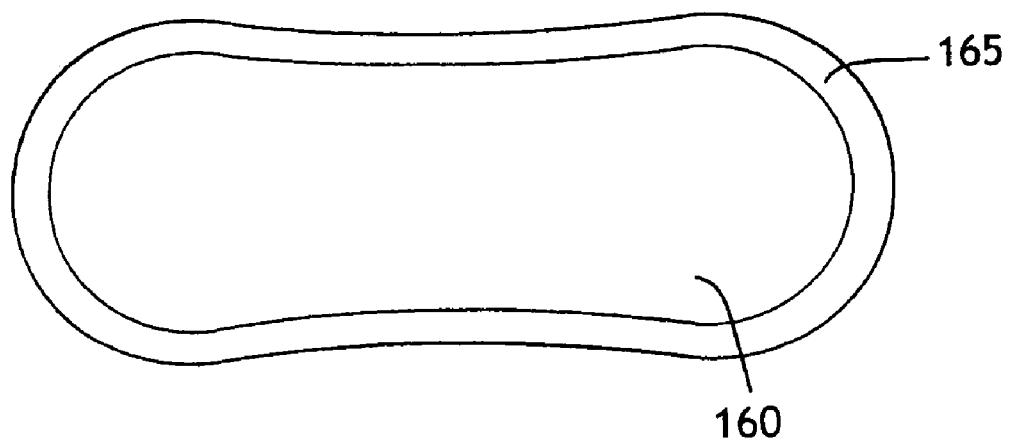
FIG. 7 is a drawing of a feminine hygiene product made in accordance with the invention.
Figure 8:
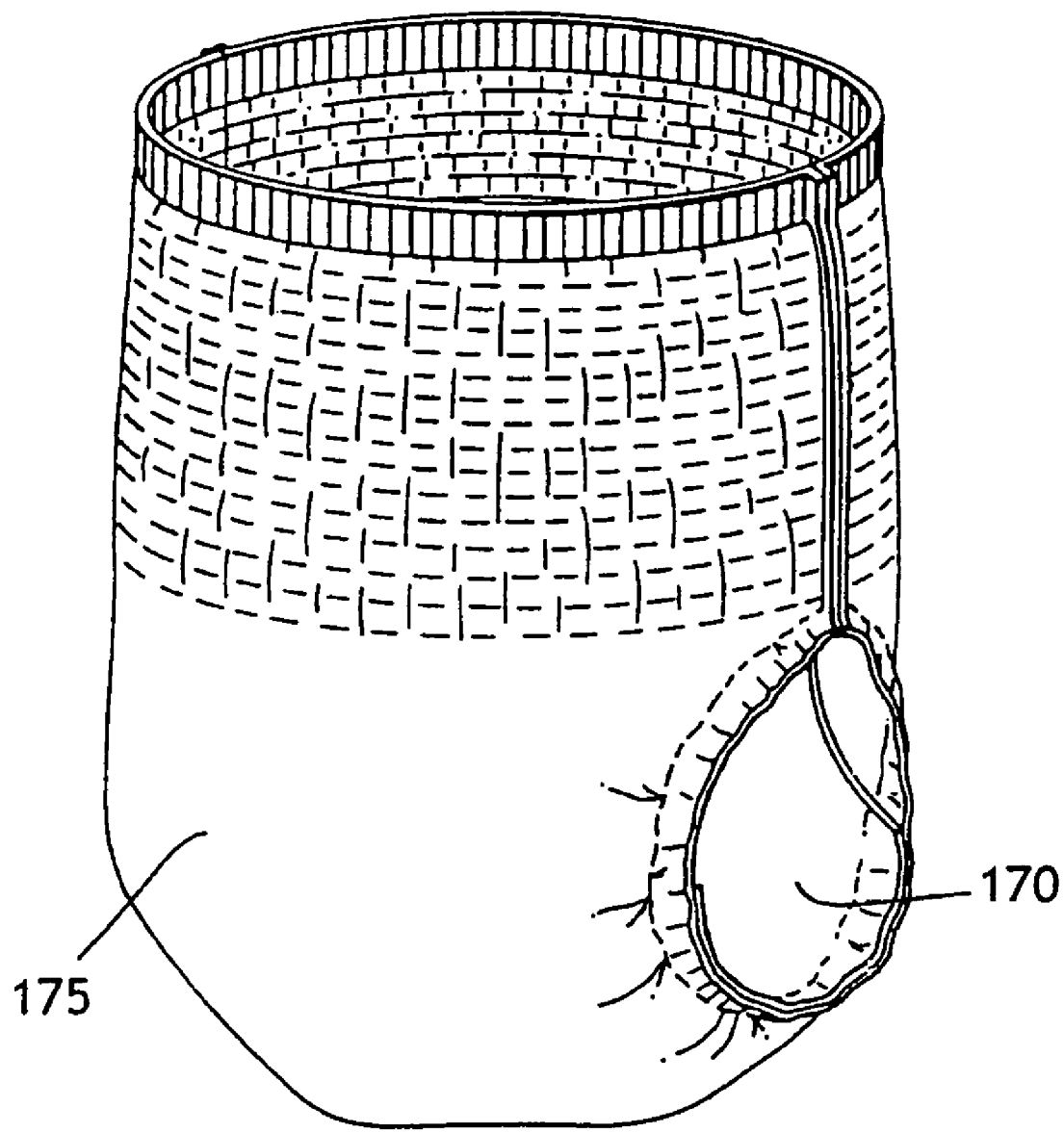
FIG. 8 is a drawing of an adult incontinence product made in accordance with the invention.

As can be seen in the various other absorbent personal care product embodiments, the inventive material may be used as an "outer cover" in a variety of product applications including a training pant, an underwear/underpant, feminine care product, and adult incontinence product. As an outercover, such material may be present in film form, or alternatively as a laminate in which a nonwoven or other sheet material has been laminated to the film layer. For instance, as can be seen in FIG. 5, the distinctive film can serve as the outer cover on both the back 135 and front portions of a training pant, separated by separate elastic side panels 140. As previously stated, such outercover may encompass the side panel areas in an alternative embodiment. As can be seen in FIG. 6, the distinctive film can serve as an outer cover in an underpant, such as either 150 or 155. As can be seen in FIG. 7, the distinctive film can serve as an outercover/backsheet 165 in a feminine care pantiliner 160. As can be seen in FIG. 8, the distinctive film can serve in an adult incontinence product as an outercover 175. Additionally such film or film laminates may serve as a sanitary napkin coversheet. Such film or film laminates may be further processed such as by being apertured and the like, before being used as base materials in such products.

A series of examples were developed to demonstrate and distinguish the attributes of the present invention. Such Examples are not presented to be limiting, but in order to demonstrate various attributes of the inventive material.

EXAMPLE 1

In Example 1 an inventive film was produced. The film layer contained calcium carbonate filler dispersed in a carrier resin. The calcium carbonate, was available from OMYA, Inc., North America of Proctor, Vt. under the designation OMYACARB® 2 SS T and had an average particle size of 2 micron, top cut of 8–10 microns and about 1% stearic acid coating. The calcium carbonate (75%) filler and carrier resin (25%), Dowlex 2517 LLDPE (melt index of 25 and density of 0.917) formed the filler concentrate compound that was then blended in a single screw conventional extruder with 33% of Septon 2004 SEPS triblock thermoplastic elastomer letdown resin to provide a final calcium carbonate concentration of 50.25% by weight. The Dowlex® polymer is available from Dow Chemical U.S.A. of Midland, Mich. The Septon polymer is available from Septon Company of America of Pasadena, Tex.

This formulation was formed into a film by casting onto a chill roll set to 104° F. at an unstretched basis weight of 64 gsm. The film was stretched 3.6 times its original length using a machine direction orienter (MDO), then retracted 35% to a stretched basis weight of 33.9 gsm. As used herein, reference to stretching the film 3.6 times means that the film which, for example, had an initial length of 1 meter if stretched 3.6 times would have a final length of 3.6 meters. The film was heated to a temperature of 125° F. and was run through the MDO at a line speed of 492 feet per minute to provide the desired stretch. The film was then annealed at a temperature of 160–180° F. across multiple rolls.

EXAMPLE 2

In Example 2, a film similar to the film of Example 1, but with 30% of Septon 2004 SEPS triblock thermoplastic elastomer letdown resin was formulated to provide a final calcium carbonate filler concentration of 52.5% by weight.

This formulation was formed into a film by casting onto a chill roll set to 99° F. at an unstretched basis weight of 64.4 gsm. The film was stretched 3.6 times its original length using a machine direction orienter (MDO), then retracted 15% to a stretched basis weight of 30.6 gsm. The film was heated to a temperature of 125° F. and was run through the MDO at a line speed of 472 feet per minute to provide the desired level of stretch. The film was then annealed at temperatures of between 160–200° F. across multiple rolls.

EXAMPLE 3

In Example 3 a film similar to the film of Example 1 was formulated, but with 40% of Septon 2004 SEPS triblock thermoplastic elastomer letdown resin, to provide a final calcium carbonate filler concentration of 45% by weight.

This formulation was formed into a film by casting onto a chill roll set to 99° F. at an unstretched basis weight of 51 gsm. The film was stretched 3.6 times its original length using a machine direction orienter (MDO) to a stretched basis weight of 40 gsm. The film was heated to a temperature of 125° F. and was run through the MDO at a line speed of 450 feet per minute to provide the desired stretch. The film was then annealed at a temperature of 180° F. across multiple rolls. A laminate made with this film will demonstrate both MD/CD stretch.

EXAMPLE 4

In Example 4 a film similar to the film of Example 1 was formulated, except the calcium carbonate compound filler concentration was 82% with carrier resin DNDA-1082 LLDPE (melt index of 155 and density of 0.933 g/cc) also from Dow Chemical U.S.A. This compound was then blended in a single screw conventional extruder with 36.5% of Septon 2004 SEPS triblock thermoplastic elastomer letdown resin to provide a final calcium carbonate concentration of 52% by weight.

This formulation was formed into a film by casting onto a chill roll set to 120° F. at an unstretched basis weight of 64.4 gsm. The film was stretched 3.6 times its original length using a machine direction orienter (MDO), then retracted 33% to a stretched basis weight of 34 gsm. The film was heated to a temperature of 125° F. and was run through the MDO at a line speed of 576 feet per minute to deliver the desired stretch. The film was then annealed at a temperature of between 170–200° F. across multiple rolls.

Comparative Example EXAMPLE 1

(Resulting Film Not Breathable)

In comparative example 1 a film similar to the film of Example 1 was formulated, except the calcium carbonate compound concentration was 75% with a carrier resin Affinity 8185 (melt index of 30 and density of 0.885 g/cc) also from Dow Chemical U.S.A. This compound was then blended in a single screw conventional extruder with 33% of Septon 2004 SEPS triblock thermoplastic elastomer letdown resin to provide a final calcium carbonate concentration of 50.25% by weight.

This formulation was formed into a film by casting onto a chill roll set to 100° F. at an unstretched basis weight of 57.5 gsm. The film was stretched 3.6 times its original length using a machine direction orienter (MDO), then retracted 36% to a stretched basis weight of 40 gsm. The film was heated to a temperature of 125° F. and was run through the MDO at a line speed of 445 feet per minute to impart the desired stretch. The film was then annealed at a temperature of between 150–180° F. across multiple rolls.

Comparative Example 2

(Letdown Resin Not an Elastomer, Resulting Film Not Elastic)

In comparative example 2, a film similar to the film of Example 1 was formulated, except the calcium carbonate compound concentration was 75% with the carrier resin Dowlex 2517 (melt index of 25 and density of 0.917 g/cc). This compound was then blended in a single screw conventional extruder with 33% of Dowlex 2047 AC (2.3 MI, 0.917 g/cc) LLDPE also from Dow Chemical U.S.A, letdown resin to provide a final calcium carbonate concentration of 50.25% by weight.

This formulation was formed into a film by casting onto a chill roll set to 102° F. at an unstretched basis weight of 45 gsm. The film was stretched 3.6 times its original length using a machine direction orienter (MDO), then relaxed 10% to a stretched basis weight of 25 gsm. The film was heated to a temperature of 125° F. and was run through the MDO at a line speed of 486 feet per minute to impart the desired stretch. The film was then annealed at a temperature of between 160–180° F. across multiple rolls.

The following Table 1 summarizes the various tests performed on the Example materials in accordance with the previously described test methods.

TABLE 1

| 70% Elongation and 2 cycle | Mocon g/m²/24 hr | 1st Load @ 50% up/gf | 1st Load @ 50% dn/gf | 2nd Load @ 50% up/gf | 2nd Load @ 50% dn/gf | Load Loss % | % Set |
|---|---|---|---|---|---|---|---|
| Example 1 | 856 | 275 | 182 | 233 | 175 | 36.1 | 8.5 |
| Example 2 | 4978 | 246 | 145 | 204 | 138 | 44.0 | 13.3 |
| Example 3 | 251 | 167 | 117 | 144 | 113 | 32.4 | 12.5 |
| Example 4 | 1490 | 213 | 143 | 183 | 137 | 35.7 | 12.5 |
| Comparative Example 1 | 85 | 274 | 169 | 219 | 160 | 42 | 15.2 |
| Comparative Example 2 | 5993 | 406 | 67 | 291 | 55 | 86 | 44.1 |

For the purposes of the Table 1, the abbreviation up/gf refers to the extension/elongation (up) tension on the cycle test in grams-force, and the abbreviation dn/gf refers to "retraction" (down) tension on the cycle test in grams-force. Elastic-type Testing was done in the CD direction, and therefore values reflect CD direction elastic performance. It is desirable that such films demonstrate load loss values less than about 50 percent. More desirably, such films should demonstrate a load loss of less than about 45 percent. Still even more desirably, such films should demonstrate a load loss of less than about 35 percent. Each of the load loss values are at 50 percent elongation in accordance with the described cycle test. Load loss is expressed in a percentage, as is set.

A filled breathable elastic film is therefore provided that provides elasticity without sacrificing breathability. Such elasticity is not compromised by the use of filler to create micropores.

What is claimed is:

1. A method for forming an elastic, breathable film comprising the steps of;
    a) filling a semi-crystalline, predominantly linear polymer with a filler to form a filled polymer such that said filled polymer contains at least 60 percent by weight filler;
    b) dry-blending a thermoplastic elastomer with said filled polymer to form a blended elastomer composition, such that said blended elastomer composition includes between about 25 and 70 percent filler by weight, between about 5 and 30 percent semi-crystalline polymer by weight, and between about 15 and 60 percent by weight elastomer;
    c) extruding the blended elastomer composition into a film, wherein said filler is not fully compounded throughout said blended elastomer composition;
    d) orienting said film in a machine direction from about 2 to about 5 times its original length, such that said film produced has a basis weight of between about 15 and 60 gsm and demonstrates a breathability greater than about 100 g/m²/24 hours and a load loss value of less than about 50 percent, at 50 percent elongation, when stretched to 70 percent elongation.

2. The method of claim 1, wherein step b, the filler is present in said blended elastomer composition between about 40 and 70 percent by weight.

3. The method of claim 1 wherein step b, the elastomer in said blended elastomer composition is present between about 15 and 50 percent by weight.

4. The method of claim 1 wherein step a, the semi-crystalline polymer is a polyethylene or polyethylene copolymer and has a melt index greater than about 5 g/10 min.

5. The method of claim 1 wherein step a, the semi-crystalline polymer is a polyethylene or polyethylene copolymer and has a melt index greater than about 10 g/10 min.

6. The method of claim 1 wherein step a, the semi-crystalline polymer has a density of greater than about 0.910 g/cc.

7. The method of claim 1 wherein step a, the semi-crystalline polymer has a density of greater than about 0.915 g/cc.

8. The method of claim 1 wherein step a, the semi-crystalline polymer has a density of about 0.917 g/cc.

9. The method of claim 1 wherein step a, the semi-crystalline polymer has a density of between about 0.917 g/cc and 0.923 g/cc.

10. The method of claim 1 wherein step a, the semi-crystalline polymer has a density of between about 0.923 g/cc and 0.960 g/cc.

11. The method of claim 1 wherein step a, the semi-crystalline polymer has a density of between about 0.917 g/cc and 0.960 g/cc.

12. The method of claim 1 wherein step a, the semi-crystalline polymer is a polypropylene or polypropylene copolymer having a MFR greater than about 10 g/10 min. and a density between about 0.89 g/cc and 0.90 g/cc.

13. The method of claim 1, wherein step a, the filled polymer contains between about 60 and 85 percent by weight filler.

14. The method of claim 1 wherein step a, the filled polymer contains greater than about 75 percent by weight filler.

15. The method of claim 1, wherein step a, the filled polymer contains greater than about 80 percent by weight filler.

16. The method of claim 2 wherein step b, the blended elastomer composition contains between about 45 and 65 percent filler by weight.

17. The method of claim 1 wherein step b, the blended elastomer composition contains between about 5 and 25 percent by weight semi-crystalline polymer.

18. The method of claim 17 wherein step b, the blended elastomer composition contains between about 10 and 25 percent by weight semi-crystalline polymer.

19. The method of claim 1 wherein step b, the blended elastomer composition contains between about 20 and 50 percent thermoplastic elastomer.

20. The method of claim 19 wherein step b, the blended elastomer composition contains between about 20 and 40 percent thermoplastic elastomer.

21. The method of claim 1 further including the step of orienting said film in the cross-machine direction.

22. An elastic, breathable film comprising:
a thermoplastic elastomer blended with a filled semi-crystalline predominantly linear polymer, said film comprising between about 25 and 70 weight percent filler, between about 5 and 30 by weight percent semi-crystalline linear polymer, and between about 15 and 60 by weight elastomeric polymer, wherein said filler is closely associated with said semi crystalline linear polymer, wherein said semi-crystalline polymer forms a predominantly non-elastic shell around the filler particles, and further wherein said film demonstrates a load loss value of less than about 50 percent, at 50 percent elongation, when stretched to 70 percent elongation, and a breathability of greater than about 100 g/m$^2$/24 hours.

23. The elastic, breathable film of claim 22 wherein the semi-crystalline polymer is a polyethylene or polyethylene copolymer and has a melt index greater than about 5 g/10 min.

24. The elastic, breathable film of claim 22 wherein the semi-crystalline polymer is a polyethylene or polyethylene copolymer and has a melt index greater than about 10 g/10 min.

25. The elastic, breathable film of claim 22 wherein the semi-crystalline polymer has a density of greater than about 0.910 g/cc.

26. The elastic, breathable film of claim 22 wherein the semi-crystalline polymer has a density of greater than about 0.915 g/cc.

27. The elastic, breathable film of claim 22 wherein the semi-crystalline polymer has a density of about 0.917 g/cc.

28. The elastic, breathable film of claim 22 wherein the semi-crystalline polymer has a density of between about 0.917 g/cc and 0.923 g/cc.

29. The elastic, breathable film of claim 22 wherein the semi-crystalline polymer has a density of between about 0.923 g/cc and 0.960 g/cc.

30. The elastic, breathable film of claim 22 wherein the semi-crystalline polymer has a density of between about 0.917 g/cc and 0.960 g/cc.

31. The elastic, breathable film of claim 22 wherein the semi-crystalline polymer is a polypropylene or polypropylene copolymer having a MFR greater than about 10 g/10 min. and a density between about 0.89 g/cc and 0.90 g/cc.

32. The elastic breathable film of claim 22, wherein said film demonstrates a percent set of less than about 50 percent.

33. The elastic breathable film of claim 22 wherein said film demonstrates a percent set of between about 20 and 50 percent.

34. The elastic breathable film of claim 22, wherein the film demonstrates a percent set of less than about 20 percent.

35. The elastic breathable film of claim 22, wherein said film demonstrates a load loss of less than about 45 percent.

36. The elastic breathable film of claim 22, wherein said film demonstrates a load loss of less than about 35 percent.

37. The elastic breathable film of claim 22, wherein said elastomer is a styrenic block copolymer.

38. The elastic breathable film of claim 22, wherein said filled polymer is a polyethylene.

39. The elastic breathable film of claim 22, wherein said breathability is greater than about 1,000 g/m$^2$/24 hours.

40. The elastic breathable film of claim 22, wherein said filler is present in said blended elastomer composition between about 40 and 70 weight percent.

41. The elastic breathable film of claim 40, wherein said filler is present in said blended elastomer composition between about 45 and 65 weight percent.

42. The elastic breathable film of claim 22, wherein said elastomer is present between about 15 and 50 percent by weight.

43. The elastic breathable film of claim 42, wherein said elastomer is present between about 20 and 50 weight percent.

44. The elastic breathable film of claim 43, wherein said elastomer is present between about 20 and 40 percent by weight.

45. The elastic breathable film of claim 22, wherein said semi-crystalline polymer is present between about 5 and 25 weight percent.

46. The elastic breathable film of claim 45, wherein said semi-crystalline polymer is present between about 10 and 25 weight percent.

47. A personal care article comprising the elastic breathable film of claim 22.

48. An outercover of a personal care article comprising the film of claim 22.

49. A recreational outdoor cover comprising the film of claim 22.

50. A disposable protective garment comprising the film of claim 22.

* * * * *